US012357457B2

(12) United States Patent
Schwarcz et al.

(10) Patent No.: US 12,357,457 B2
(45) Date of Patent: Jul. 15, 2025

(54) VALVE DIAMETER AND FORCE MONITORING OF A PROSTHETIC HEART VALVE

(71) Applicant: Edwards Lifesciences Corporation, Irvine, CA (US)

(72) Inventors: Elazar Levi Schwarcz, Netanya (IL); Oren Cohen, Kadima (IL); Tomer Saar, Pardes Hanna-Karkur (IL); Yair A. Neumann, Moshav Sede Varburg (IL); Ofir Witzman, Kfar Saba (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 864 days.

(21) Appl. No.: 17/241,577

(22) Filed: Apr. 27, 2021

(65) Prior Publication Data

US 2021/0282921 A1    Sep. 16, 2021

Related U.S. Application Data

(63) Continuation of application No. PCT/US2019/058368, filed on Oct. 28, 2019.
(Continued)

(51) Int. Cl.
*A61F 2/24* (2006.01)
*A61B 5/00* (2006.01)
(Continued)

(52) U.S. Cl.
CPC ............ *A61F 2/243* (2013.01); *A61B 5/0048* (2013.01); *A61B 5/1126* (2013.01);
(Continued)

(58) Field of Classification Search
CPC .................... A61F 2/243; A61F 2/9517; A61F 2250/0096; A61F 2002/9505;
(Continued)

(56) References Cited

U.S. PATENT DOCUMENTS 3,409,013 A    11/1968 Berry
3,548,417 A    12/1970 Kisher
(Continued)

FOREIGN PATENT DOCUMENTS

DE    0144167 C    9/1903
DE    2246526 A1    3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Techniqeu in Closed Chest Pig," European Heart Journal, No. 13. pp. 704-708. 1992.
(Continued)

*Primary Examiner* — Jerrah Edwards
*Assistant Examiner* — Kia Xiong White
(74) *Attorney, Agent, or Firm* — Klarquist Sparkman, LLP; Joel B. German

(57) ABSTRACT

A delivery apparatus including a measurement device to monitor the real-time diameter of a prosthetic heart valve can include a handle, at least one first actuator extending from the handle and being configured to apply a distally directed force to a proximal end portion of a prosthetic heart valve, at least one second actuator extending from the handle and being configured to apply a proximally directed force to a distal end portion of a prosthetic heart valve, a sensor, and first and second motion-transmitting members coupled to the first and second actuators, respectively, and having proximal ends coupled to the sensor, wherein the sensor senses relative movement between the motion-transmitting members upon actuation of the first and second actuators to determine the diameter of the prosthetic heart valve as it expands from a radially compressed configuration to a radially expanded configuration.

24 Claims, 8 Drawing Sheets

Related U.S. Application Data

(60) Provisional application No. 62/893,084, filed on Aug. 28, 2019, provisional application No. 62/752,898, filed on Oct. 30, 2018.

(51) Int. Cl.
*A61B 5/11* (2006.01)
*A61F 2/95* (2013.01)

(52) U.S. Cl.
CPC .... *A61F 2/9517* (2020.05); *A61B 2562/0214* (2013.01); *A61B 2562/0238* (2013.01); *A61F 2250/0096* (2013.01)

(58) Field of Classification Search
CPC ....... A61F 2002/9665; A61F 2250/001; A61B 5/0048; A61B 5/1126; A61B 2562/0214; A61B 2562/0238
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |

(56) References Cited

U.S. PATENT DOCUMENTS

| | | |
|---|---|---|
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,202 B2 | 2/2014 | Alon et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0237321 A1 | 12/2004 | Rudko et al. |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1* | 10/2014 | Cartledge ............ A61F 2/2412 623/1.11 |
| 2014/0330372 A1 | 11/2014 | Weston et al. |
| 2014/0343670 A1 | 11/2014 | Bakis et al. |
| 2014/0343671 A1 | 11/2014 | Yohanan et al. |

(56) References Cited

U.S. PATENT DOCUMENTS

| | | |
|---|---|---|
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0060057 A1 | 2/2019 | Cohen et al. |
| 2019/0105153 A1 | 4/2019 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 01176510 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |
| WO | 2016100806 A1 | 6/2016 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: In vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

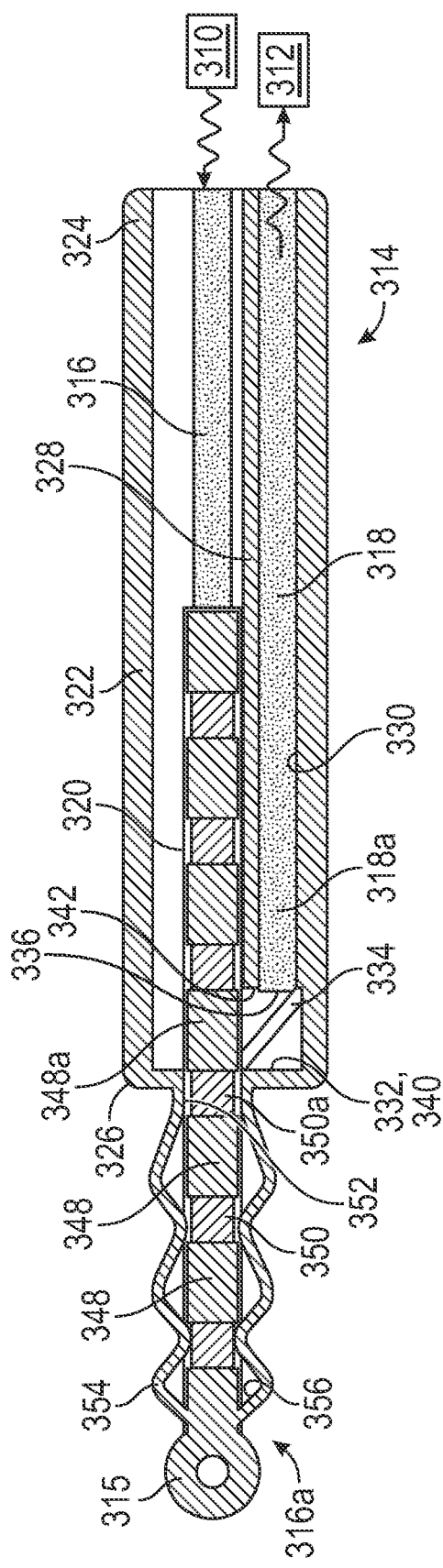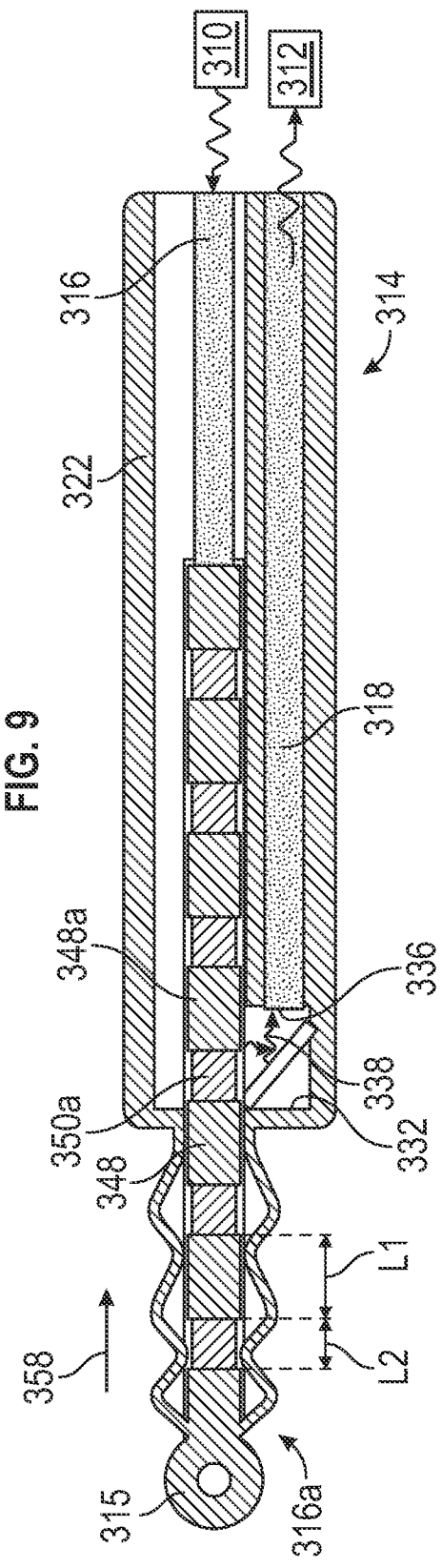
FIG. 9
FIG. 10

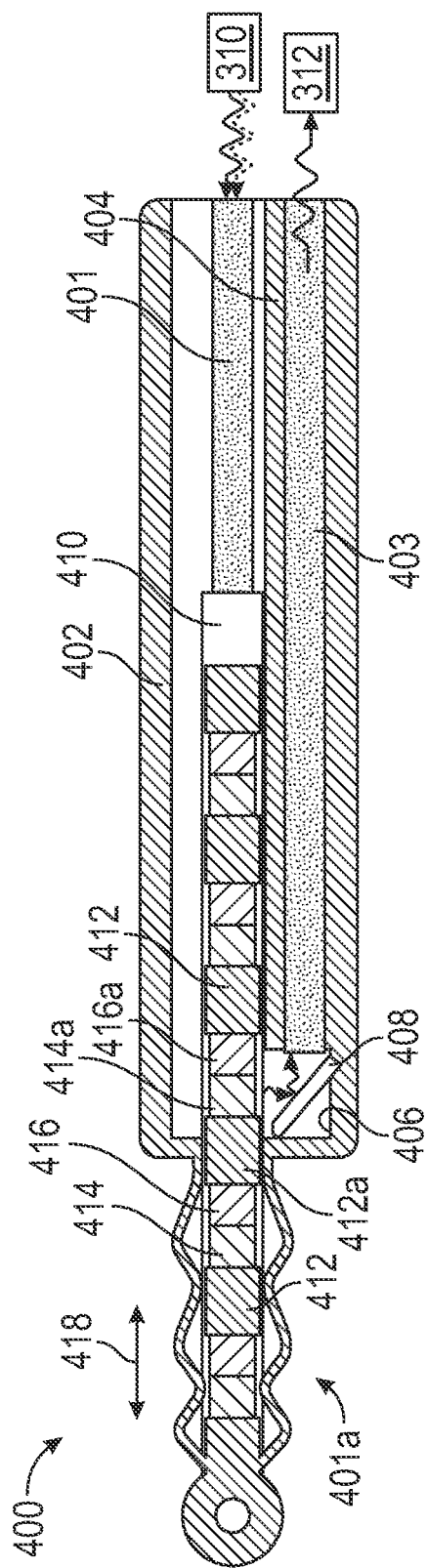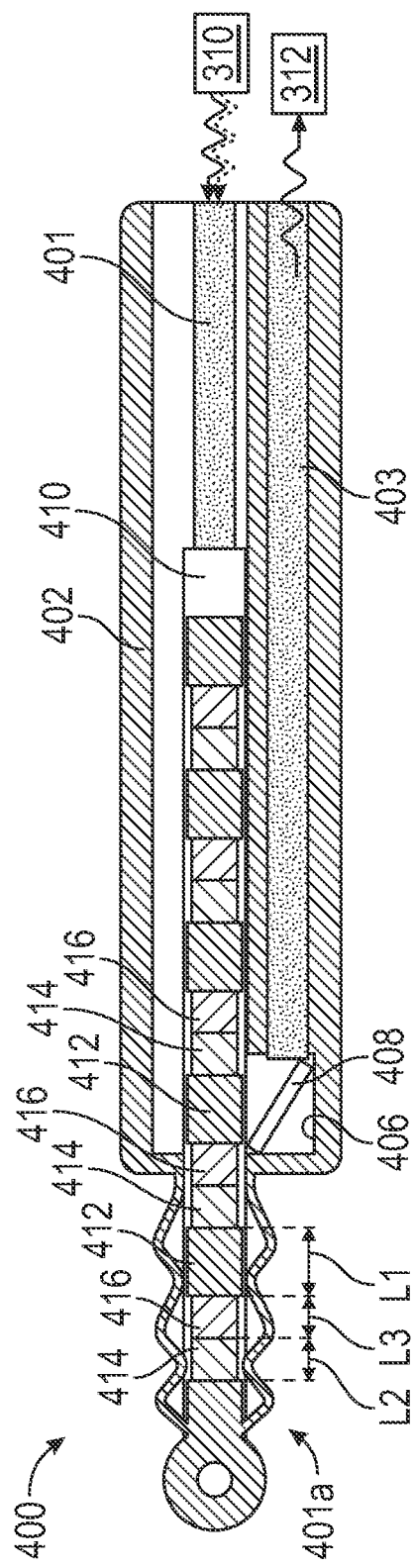

VALVE DIAMETER AND FORCE MONITORING OF A PROSTHETIC HEART VALVE

CROSS-REFERENCE TO RELATED APPLICATIONS

This application is a continuation of International Application No. PCT/US2019/058368, filed Oct. 28, 2019, which claims the benefit of U.S. Provisional Application No. 62/893,084 filed on Aug. 28, 2019, and which also claims the benefit of U.S. Provisional Application No. 62/752,898 filed on Oct. 30, 2018. The entirety of each of the foregoing applications is hereby incorporated herein by reference.

FIELD

The present disclosure relates to measurement devices for monitoring the diameter and radial force of implantable, mechanically expandable prosthetic devices, such as prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

When deploying a prosthetic valve, it is important to avoid exerting excessive radial force on the native annulus of the patient, which can rupture the native heart valve annulus. To avoid damage to the native tissue, it is desirable to monitor the diameter of the prosthetic valve and/or the radial force exerted by the prosthetic valve during deployment.

Unfortunately, known methods for measuring diameter and radial force suffer from several problems. For example, measurement devices placed in or around the prosthetic valve can affect the crimp profile of the valve. Measurement methods relying on measuring the displacement of an actuation mechanism fail to account for factors such as compression of the delivery device and/or elongation of the actuation mechanism under tension. Thus, there remains a need for improved devices and methods for monitoring the diameter and radial force of transcatheter heart valves during implantation.

SUMMARY

Described herein are embodiments of measurement devices for use with delivery assemblies that implant prosthetic devices. The measurement devices are primarily intended to monitor the real-time diameter and/or radial force of a prosthetic device. The measurement devices can be used with a delivery apparatus to help ensure proper implantation of a prosthetic device within a defective native valve.

In a representative embodiment, a medical assembly can comprise a prosthetic heart valve and a delivery apparatus. The prosthetic heart valve can be radially expandable and compressible between a radially compressed configuration and a radially expanded configuration. The delivery apparatus can comprise a handle, at least one first actuator extending from the handle and coupled to a proximal end portion of the prosthetic valve, and at least one second actuator extending from the handle and coupled to a distal end portion of the prosthetic valve. The at least one first actuator is configured to apply a distally directed force to the proximal end portion of the prosthetic valve. The at least one second actuator is configured to apply a proximally directed force to the distal end portion of the prosthetic valve. In some embodiments, the at least one second actuator of the delivery apparatus can extend through the at least one first actuator.

The delivery apparatus further comprises a sensor, a first motion-transmitting member, and a second motion-transmitting member. The first motion-transmitting member has a distal end portion coupled to the at least one first actuator and a proximal end portion coupled to the sensor. The second motion-transmitting member has a distal end portion coupled to the at least one second actuator and a proximal end coupled to the sensor. The prosthetic heart valve is radially expandable from the radially compressed configuration to the radially expanded configuration upon actuation of the at least one first actuator and/or the at least one second actuator to apply a distally directed force and/or a proximally directed force, respectively, to the prosthetic heart valve. The sensor senses relative movement between the first and second motion-transmitting members upon actuation of the at least one first actuator and the at least one second actuator to determine the diameter of the prosthetic heart valve as it is expanded.

In some embodiments, the sensor is a linear displacement sensor. In some embodiments, the linear displacement sensor can be a linear variable differential transformer (LVDT), an optical linear encoder, or a combination thereof.

The delivery apparatus can further comprise a load cell coupled to a proximal end portion of the at least one second actuator. The load cell is configured to measure tensile force in the second actuator as the prosthetic valve expands. In some embodiments, the load cell can be disposed within the handle. In some embodiments, the load cell can be a compression load cell, a strain gauge load cell, a piezoelectric load cell, a pneumatic load cell, a hydraulic load cell, or a combination thereof.

The medical assembly can further comprise a control unit in communication with the sensor and/or the load cell. The control unit is configured to calculate at least one of the real-time radial force and the real-time diameter of the prosthetic valve. In some embodiments, the control unit can comprise a display configured to display to a user at least one of the real-time radial force and the real-time diameter of the prosthetic valve. In some embodiments, the control unit can control the first and second actuators to expand the prosthetic valve according to a preprogrammed expansion algorithm.

In some embodiments, the prosthetic heart valve can comprise at least one push-pull actuator assembly. The push-pull actuator assembly can comprise a first member attached to the proximal end portion of the prosthetic heart valve and a second member attached to a distal end portion of the prosthetic heart valve. The first actuator of the delivery apparatus can be releasably coupled to the first member and the second actuator of the delivery apparatus can be releasably coupled to the second member.

In some embodiments, the first and second motion-transmitting members can comprise first and second wires. In some embodiments, the first and second motion-transmitting members extend the majority of the lengths of the first and second actuators, respectively. In some embodiments, the distal end portions of the first and second motion-transmitting members are affixed to the first and second actuators, respectively, at respective locations adjacent the prosthetic heart valve.

In another representative embodiment, a delivery apparatus comprises a handle, at least one first actuator, and at least one second actuator. The first actuator extends from the handle and is configured to apply a distally directed force to a proximal end portion of a prosthetic heart valve. The second actuator extends from the handle and is configured to apply a proximally directed force to a distal end portion of the prosthetic heart valve. The proximally and/or distally directed forces applied by the actuators can be used to radially expand the prosthetic heart valve.

The delivery apparatus further comprises a first motion-transmitting member and a second motion-transmitting member, a sensor, and a control unit in communication with the sensor. The first motion-transmitting member has a distal end portion coupled to the first actuator and a proximal end portion coupled to the sensor. The second motion-transmitting member has a distal end portion coupled to the second actuator and a proximal end portion coupled to the sensor. The sensor is configured to sense relative movement between the first and second motion-transmitting members upon actuation of the first and/or second actuators. In some embodiments, the sensor is a linear displacement sensor. The control unit determines the real-time diameter of the prosthetic heart valve as it expands from a radially compressed configuration to a radially expanded configuration based on the relative movement between the first and second motion-transmitting members.

In some embodiments, the delivery apparatus can further comprise a load cell operatively coupled to the second actuator. The load cell can be configured to measure tension in the second actuator as the prosthetic valve expands. In some embodiments, the control unit can be configured to calculate the real-time radial force of the prosthetic valve based on the tension of the second actuator. In some embodiments, the control unit can further comprise a display configured to display to a user at least one of the real-time radial force and the real-time diameter of the prosthetic valve.

In some embodiments, the first and second motion-transmitting members can comprise first and second wires extending the majority of the lengths of the first and second actuators.

A representative method for implanting a prosthetic valve comprises inserting into the body of a patient a distal end portion of a delivery apparatus and a radially compressed prosthetic heart valve coupled to the distal end portion of the delivery apparatus. The delivery apparatus comprises a handle, at least one first actuator, and at least one second actuator. The first actuator extends from the handle and is configured to apply a distally directed force to the proximal end portion of the prosthetic valve. The second actuator extends from the handle and is configured to apply a proximally directed force to the distal end portion of the prosthetic valve. The delivery apparatus further comprises a sensor, a first motion-transmitting member, and a second motion-transmitting member. The first motion-transmitting member has a distal end coupled to the first actuator and a proximal end coupled to the sensor. The second motion-transmitting member has a distal end coupled to the second actuator and a proximal end coupled to the sensor.

The method further comprises advancing the delivery apparatus distally until the prosthetic valve is disposed at a selected implantation site and radially expanding the prosthetic heart valve by at least one of advancing the first actuator distally and retracting the second actuator proximally. As the prosthetic heart valve is expanded, the method further comprises using the sensor to sense the relative displacement between the proximal end portions of the first and second motion-transmitting members and calculating a real-time diameter of the prosthetic heart valve based on the relative displacement between the first and second motion-transmitting members.

In some embodiments, the method can further comprise measuring the radial force of the prosthetic valve against surrounding tissue during expansion of the prosthetic heart valve. The radial force can be measured using a load cell coupled to the at least one second actuator. The method can further comprise displaying at least one of the real-time diameter and the radial force of the prosthetic heart valve on a display unit.

In another representative embodiment, a delivery apparatus comprises a handle, at least one first actuator, and at least one second actuator. The first actuator extends from the handle and is configured to apply a distally directed force to a proximal end portion of a prosthetic heart valve. The second actuator extends from the handle and is configured to apply a proximally directed force to a distal end portion of the prosthetic heart valve. The distally and/or proximally directed forces are used to radially expand the prosthetic heart valve. The delivery apparatus further comprises a load cell operatively connected to either a proximal end portion of the first actuator or a proximal end portion of the second actuator. The load cell is configured to measure a load on either the first actuator or the second actuator. The delivery apparatus further comprises a control unit in communication with the load cell. The control unit is configured to calculate the radial force applied by the prosthetic heart valve against the surrounding tissue based on the load measured by the load cell.

In some embodiments, the delivery apparatus can further comprise a sensor, a first motion transmitting member, and a second motion transmitting member. The sensor can be in communication with the control unit. The first motion-transmitting member can have a distal end portion coupled to the at least one first actuator and a proximal end coupled to the sensor. The second motion-transmitting member can have a distal end portion coupled to the at least one second actuator and a proximal end coupled to the sensor. The sensor can sense relative movement between the first and second motion-transmitting members upon actuation of the first and second actuators. The control unit can determine a real-time diameter of the prosthetic heart valve as it expands from a radially compressed configuration to a radially expanded configuration based on the relative movement between the first and second motion-transmitting members.

In yet another representative embodiment, a prosthetic heart valve assembly can comprise a prosthetic heart valve movable between a radially compressed configuration and a radially expanded configuration, and a delivery apparatus. The delivery apparatus can comprise a handle comprising a light source and a receiving element, a first actuator extending from the handle and coupled to a first portion of the prosthetic heart valve, wherein the first actuator is configured to apply a distally directed force to the first portion of the prosthetic valve, a second actuator extending from the handle and coupled to a second portion of the prosthetic valve, wherein the actuator is configured to apply a proximally directed force to the second portion of the prosthetic valve, a sensor, a first optical fiber, and a second optical fiber. The sensor can be coupled to a distal end portion of the first actuator and can comprise a housing. The first optical fiber can extend through the housing and can have a proximal end portion coupled to the light source and a distal end portion coupled to the second actuator. The second optical fiber can have a proximal end portion coupled to the receiving element and a distal end portion extending into the housing. The prosthetic heart valve can be radially expandable from the radially compressed configuration to the radially expanded configuration upon applying the distally directed force and the proximally directed force to the prosthetic heart valve with the first and second actuators, respectively. The sensor can sense relative movement between the first optical fiber and the housing upon actuation of at least one of the first actuator and the second actuator to determine the diameter of the prosthetic heart valve as it is expanded.

In some embodiments, the housing can define a recess and the sensor further comprises an optical coupler disposed within the recess and configured to couple light emitted by the first fiber into the second fiber. In some embodiments, the optical coupler comprises a reflective metal. In other embodiments, the optical coupler can comprise a cut portion of the second fiber.

In some embodiments, the first fiber comprises a plurality of alternating marked portions and exposed portions, the exposed portions being configured to emit light and the marked portions being configured to prevent light from being emitted. As the first fiber moves relative to the housing the alternating marked and exposed portions can produce a light pattern. The sensor can be configured to determine the diameter of the prosthetic valve as it is expanded based at least in part on the light pattern.

In some embodiments, the first fiber can comprise a plurality of marked portions, first filtered portions, and second filtered portions arranged in a selected order. The marked portions can be configured to prevent light from being emitted by the first fiber, the first filtered portions can be configured to allow a first wavelength of light to be emitted, and the second filtered portions can be configured to allow a second wavelength of light to be emitted. As the first fiber moves relative to the housing in a first direction the marked portions, first filtered portions, and second filtered portions produce a first light pattern. As the first fiber moves relative to the housing in a second direction the marked portions, first filtered portions, and second filtered portions produce a second light pattern. The sensor can determine the direction of movement of the second actuator based on at least one of the first and second light patterns. In some embodiments, the sensor is configured to determine the diameter of the prosthetic valve as it is expanded based at least in part on the first and second light patterns.

In some embodiments, the assembly further comprises a control unit operatively coupled to the sensor. The control unit can be configured to calculate the real-time diameter of the prosthetic valve.

In some embodiments, the sensor further comprises a sealing member coupled to a distal end portion of the housing and configured to prevent bodily fluids from entering the housing, the sealing member defining a lumen into which the distal end portion of the first fiber extends.

In another representative embodiment, a delivery apparatus for a prosthetic heart valve can comprise a handle, a light source configured to emit light, a receiving element configured to receive light, at least one first actuator and at least one second actuator extending from the handle, the first actuator being configured to apply a distally directed force to a first portion of a prosthetic heart valve and the second actuator being configured to apply a proximally directed force to a second portion of the prosthetic heart valve to radially expand the prosthetic heart valve, a sensor, a control unit in communication with the sensor, a first optical fiber, and a second optical fiber. The first optical fiber can be configured to produce a light pattern as the first fiber moves relative to the sensor. The first fiber can extend through the sensor and have a distal end portion coupled to the second actuator and a proximal end portion coupled to the light source. The second optical fiber can have a distal end portion coupled to the sensor and a proximal end portion coupled to the receiving element. Actuation of the second actuator can cause corresponding movement of the first optical fiber relative to the sensor. The sensor can sense the light pattern and the control unit can determine a real-time diameter of the prosthetic heart valve as it moves between a radially compressed configuration and a radially expanded configuration based at least in part on the light pattern.

In some embodiments, the distal end portion of the first fiber comprises a plurality of alternating marked portions and exposed portions configured to produce the light pattern.

In other embodiments, the distal end portion of the first fiber comprises a plurality of marked portions, first filtered portion, and second filtered portions disposed in a selected order, wherein movement of the second actuator in a first direction produces a first light pattern and movement of the second actuator in a second direction opposite the first direction produces a second light pattern. The control unit can determine a real-time diameter of the prosthetic heart valve based at least in part on at least one of the first light pattern and the second light pattern.

In some embodiments, the first fiber can comprise a core and a cladding and the distal end portion of the first fiber can comprise a portion of the first fiber wherein the cladding has been removed and the core has been abraded. In other embodiments, the distal end portion of the first fiber can comprise a polymer member.

In a representative embodiment, a method of implanting a prosthetic heart valve can include inserting into the body of a patient a distal end portion of a delivery apparatus and a prosthetic heart valve coupled to the distal end portion of the delivery apparatus in a radially compressed configuration. The delivery apparatus can comprise a handle having a light source and a receiver element, a first actuator extending from the handle and configured to apply a distally directed force to a first portion of the prosthetic valve, a second actuator extending from the handle and configured to apply a proximally directed force to a second portion of the prosthetic valve, a sensor, a first optical fiber, the first optical fiber extending through the sensor and having a distal end portion coupled to the second actuator and a proximal end portion coupled to the light source, and a second optical fiber having a distal end portion coupled to the sensor and a proximal end portion coupled to the receiving element. The method can further include advancing the delivery apparatus distally until the prosthetic heart valve is disposed at a selected implantation site, and radially expanding the prosthetic heart valve by at least one of advancing the first actuator distally and retracting the second actuator proximally to produce relative movement between the first optical fiber and the sensor such that the first optical fiber produces a light pattern. As the prosthetic heart valve is expanded, the receiving element can determine the light pattern and calculate a real-time diameter of the prosthetic heart valve based at least in part on the light pattern.

In some embodiments, the method can further comprise radially collapsing the prosthetic heart valve by at least one of retracting the first actuator proximally and advancing the second actuator distally such that the first fiber moves relative to the sensor to produce a second light pattern. As the prosthetic heart valve is collapsed, the receiving element can determine the second light pattern and can calculate the real-time diameter of the prosthetic heart valve based at least in part on the light pattern and the second light pattern.

In other embodiments, the method can further comprise displaying the real-time diameter of the prosthetic heart valve on a display unit.

The various innovations of this disclosure can be used in combination or separately. This summary is provided to introduce a selection of concepts in a simplified form that a further described below in the detailed description. This summary is not intended to identify key features or essential features of the claimed subject matter. The foregoing and other objects, features, and advantages of the disclosure will become more apparent from the following detailed description, which proceeds with reference to the accompanying figures.

BRIEF DESCRIPTION OF THE DRAWINGS

FIG. 9 is a cross-sectional side view of a portion of the delivery apparatus of FIG. 8.

FIG. 10 is a cross-sectional side view a portion of the delivery apparatus of FIG. 8 in a partially extended position.

FIG. 11 is a cross-sectional side view of a portion of another exemplary embodiment of a delivery apparatus.

FIG. 12 is a cross-sectional side view of a portion of the delivery apparatus of FIG. 11 in a partially extended position.

DETAILED DESCRIPTION

Exemplary Embodiments

Described herein are embodiments of measurement devices that are primarily intended to monitor the real-time diameter and/or radial force of a prosthetic heart valve. The measurement devices can be used in conjunction with a delivery apparatus to help implant a prosthetic heart valve more precisely and safely than known delivery apparatuses.

Prosthetic valves disclosed herein can be radially compressible and expandable between a radially compressed configuration and a radially expanded configuration. Thus, the prosthetic valves can be crimped on an implant delivery apparatus in the radially compressed configuration during delivery, and then expanded to the radially expanded configuration once the prosthetic valve reaches the implantation site.

Figure 1:
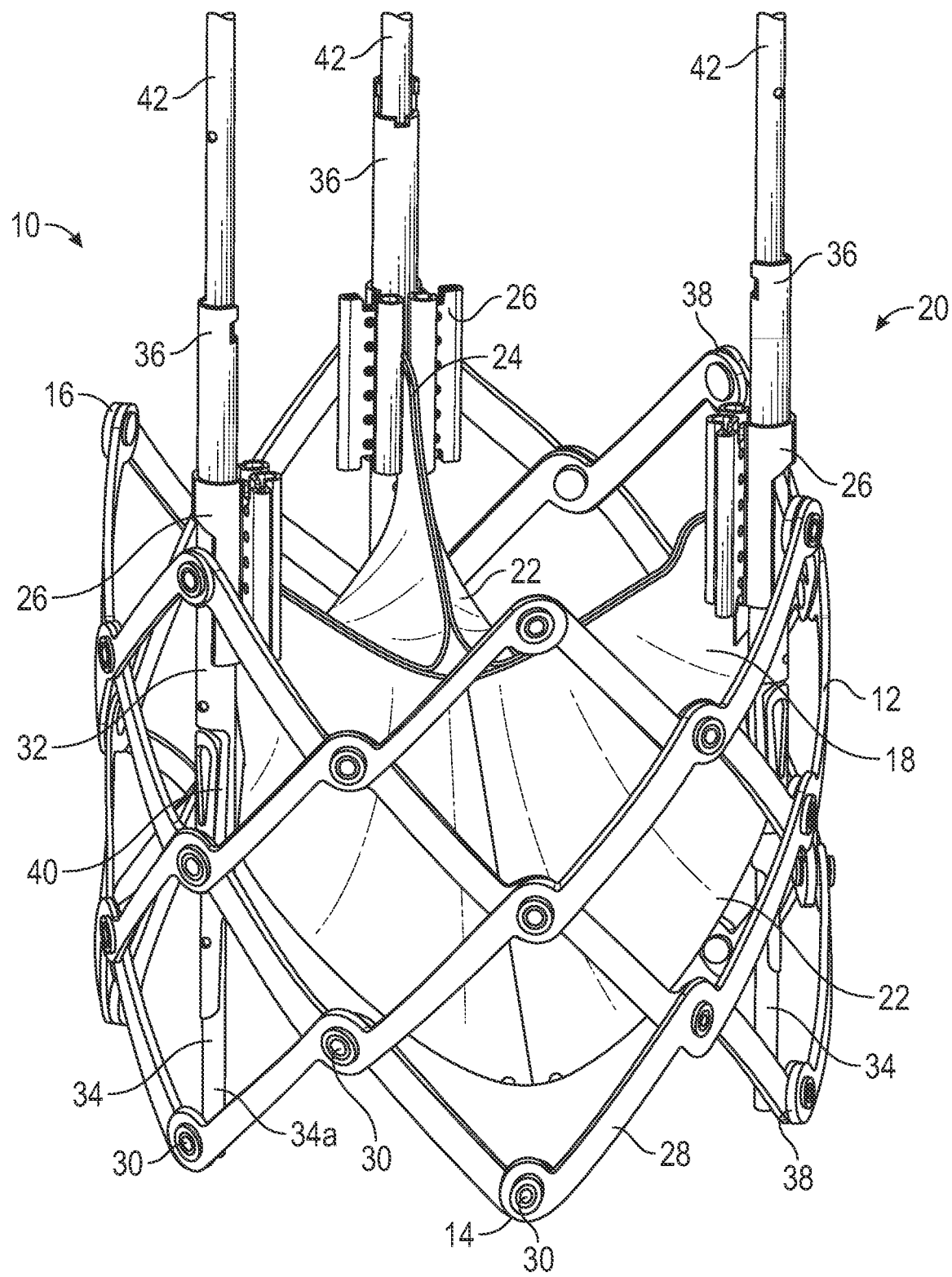
FIG. 1 is a perspective view of an exemplary embodiment of a prosthetic heart valve.

FIG. 1 shows an exemplary prosthetic valve 10, according to one embodiment. The prosthetic valve 10 can be radially compressible and expandable between a radially compressed configuration for delivery into a patient (see e.g., FIG. 3) and a radially expanded configuration (see e.g., FIGS. 1 and 4). In particular embodiments, the prosthetic valve 10 can be implanted within the native aortic annulus, although it also can be implanted at other locations in the heart, including within the native mitral valve, the native pulmonary valve, and the native tricuspid valve. The prosthetic valve 10 can include an annular stent or frame 12 having a first end 14 and a second end 16.

In the depicted embodiments, the first end 14 is an inflow end and the second end 16 is an outflow end. The outflow end 16 can be coupled to a delivery apparatus for delivering and implanting the prosthetic valve within the native aortic valve is a transfemoral, retrograde delivery approach. In other embodiments, the inflow end 14 can be coupled to the delivery apparatus, depending on the particular native valve being replaced and the delivery technique that is used (e.g., transfemoral, transapical, etc.).

The prosthetic valve 10 can also include a valvular structure 18 which is coupled to the frame 12 and configured to regulate the flow of blood through the prosthetic valve 10 from the inflow end to the outflow end. The prosthetic valve 10 can further include a plurality of actuators 20 mounted to and equally spaced around the inner surface of the frame 12. Each of the actuators 20 can be configured to form a releasable connection with one or more respective actuators of a delivery apparatus, as further described below.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). The leaflets 22 can be arranged to form commissures 24, which can be, for example, mounted to respective actuators 20. Further details regarding transcatheter prosthetic heart valves, including the manner in which the valvular structure can be coupled to the frame 12 of the prosthetic valve 10, can be found, for example, in U.S. Pat. Nos. 6,730,118, 7,393,360, 7,510,575, 7,993,394, and 8,652,202, and U.S. Patent Publication No. 2018/0325665 all of which are incorporated herein by reference in their entireties.

In some embodiments, the prosthetic valve 10 can include a plurality of commissure support elements configured as commissure clasps or clamps 26. In the illustrated configuration, the prosthetic valve includes a commissure clamp 26 positioned at each commissure 24 and configured to grip adjacent portions of two leaflets 22 at each commissure 24 at a location spaced radially inwardly of the frame 12. Each clamp 26 can be mounted on an actuator 20 as shown. In alternative embodiments, the commissure supports elements (such as clamps 26) can be mounted to the struts 28 of the frame, or alternatively, the commissures 24 can be mounted (e.g., sutured) directly to the struts of the frame. Further details of the commissure clamps 26 and other techniques for mounting the commissures of a valve assembly to a frame can be found in U.S. Patent Publication No. 2018/0325665.

Although not shown, the prosthetic valve 10 can also include one or more skirts or sealing members. For example, the prosthetic valve 10 can include an inner skirt mounted on the inner surface of the frame. The inner skirt can function as a sealing member to prevent or decrease perivalvular leakage, to anchor the leaflets 22 to the frame, and/or to protect the leaflets against damage caused by contact with the frame during crimping and during working cycles of the prosthetic valve. The prosthetic valve 10 can also include an outer skirt mounted on the outer surface of the frame 12. The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic valve 10 when the prosthetic valve 10 is in the expanded configuration. In other implementations, the struts 28 can be offset by a different amount than depicted in FIG. 1, or some or all of the struts 28 can be positioned parallel to the longitudinal axis of the prosthetic valve 10.

In the illustrated embodiment, the struts 28 are pivotably coupled to one another at one or more pivot joints along the length of each strut. For example, in the illustrated configuration, each of the struts 28 can be formed with apertures (see e.g., apertures 114 in FIG. 4) at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. Patent Publication Nos. 2018/0153689; 2018/0344456; 2019/0105153; 2019/0060057; all of which are incorporated herein by reference. Additional examples of expandable prosthetic valves that can be used with the delivery apparatuses disclosed herein are described in U.S. Publication No. 2015/0135506 and 2014/0296962, which are incorporated herein by reference.

Referring still to FIG. 1, in some embodiments, the prosthetic valve 10 can comprise one or more actuators 20 configured to produce radial expansion and compression of the frame. The one or more actuators in the illustrated embodiment comprise one or more push-pull mechanisms 32 coupled to the frame 12. In the illustrated embodiment, the prosthetic valve 10 has three push-pull mechanisms 32, however, in other embodiments a greater or fewer number of push-pull mechanisms 32 can be used.

Each push-pull mechanism 32 can generally comprise an inner member 34, such as an inner tubular member, and an outer member 36 disposed about the inner member 34. The inner members 34 and the outer members 36 can be movable longitudinally relative to each other in a telescoping manner to radially expand and contract the frame 12, as further described in U.S. Patent Publication Nos. 2018/0153689 and 2018/0325665, which are incorporated herein by reference. The inner members 34 can be, for example, rods, cables, wires, or tubes. The outer members 36 can be, for example, tubes or sheaths having sufficient rigidity such that they can apply a distally directed force to the frame without bending or buckling.

The inner members 34 can have distal end portions 34a coupled to the inflow end 14 of the frame 12 (e.g., with a coupling element such as a pin member 30). In the illustrated embodiment, each of the inner members 34 are coupled to the frame at respective apices 38 at the inflow end 14 of the frame 12. For example, the distal end portion 34a of each inner member 34 can be pivotably connected to the rivet or pin 30 that connects the two struts at the adjacent apex 38. The outer members 36 can be coupled to apices 38 at the outflow end 16 of the frame 12 at, for example, a midportion of the outer member 36, as shown in FIG. 1, or at a proximal end portion of the outer member, as desired. The outer members 36 can be pivotably connected to the rivet or pin 30 that connects the two struts at the adjacent apex 38.

The inner member 34 and the outer member 36 can telescope relative to each other between a fully contracted state (corresponding to a fully radially expanded state of the prosthetic valve) and a fully extended state (corresponding to a fully radially compressed state of the prosthetic valve). In the fully extended state, the inner member 34 is fully extended from the outer member 36. In this manner, the push-pull mechanisms 32 allow the prosthetic valve to be fully expanded or partially expanded to different diameters and retain the prosthetic valve in the partially or fully expanded state.

In use, a delivery apparatus can be releasably coupled to the push-pull mechanisms 32 of prosthetic valve 10. For example, the delivery apparatus can have one or more actuator assemblies that are releasably coupled to respective push-pull mechanisms 32 of the prosthetic valve. The actuators of the delivery apparatus can be configured to transfer pushing and/or pulling forces from a handle of the delivery apparatus to the push-pull mechanisms 32 of the prosthetic valve. Each of the actuator assemblies of the delivery apparatus can include an inner member 42 that is releasably coupled to a respective inner member 34 of a push-pull mechanism 32. Each actuator assembly of the delivery apparatus can also include an outer member (not shown) that is releasably coupled to a respective outer member 36 of a push-pull mechanism 32.

Once coupled to the delivery apparatus, the prosthetic valve 10 can then be radially collapsed (see e.g., FIG. 3) and the distal end portion of the delivery apparatus, along with the radially collapsed valve, can be inserted into a patient. Once the prosthetic valve 10 is at the desired implantation site, the prosthetic valve can be radially expanded (see e.g., FIG. 4). In some embodiments, as shown in FIG. 1, the push-pull mechanisms 32 can comprise one or more locking mechanisms 40, allowing the frame 12 to maintain an expanded diameter after the prosthetic valve is released from the delivery apparatus. Additional details of the locking mechanism can be found in Patent Publication No. 2018/0153689

Figure 2:
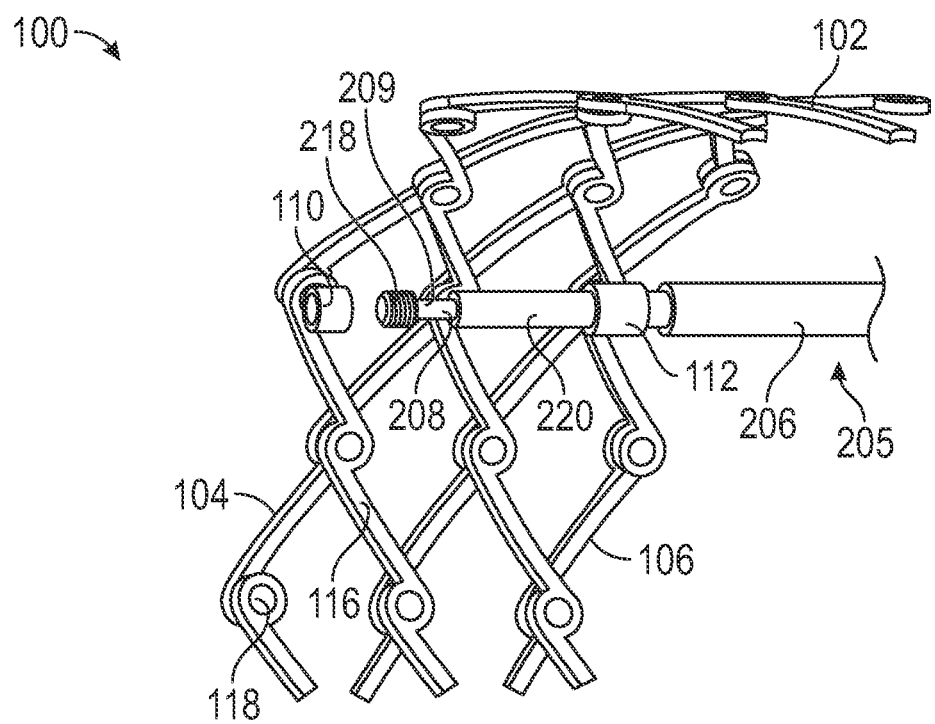
FIG. 2 is a perspective view of a portion of another exemplary embodiment of a prosthetic heart valve.

FIG. 2 illustrates another embodiment of a prosthetic valve 100 comprising a frame 102. The prosthetic valve 100 can include leaflets 22 and inner and/or outer skirts as previously described, although these components are omitted for purposes of illustration. The frame 102 comprises a plurality of struts 116 formed with apertures 114 (see FIG. 4) and pivot members 118 (e.g., pins or rivets) connecting the struts to each other form a plurality of pivot joints. The frame 102 can have the same construction as the frame 12, except that the frame 102 includes struts 116 that are longer than struts 28 of frame 12. The longer struts 116 form more pivot joints along the length of each strut and more openings or cells of the frame compared to the struts 28.

The prosthetic valve 100 is configured to be releasably coupled to one or more actuator assemblies 205 of a delivery apparatus 200 (further described below) to produce radial expansion and compression of the frame 102. To such ends, the prosthetic valve 100 can include one or more nuts or threaded sleeves 110 affixed to the frame 102, such as at an inflow portion 104 of the frame 102. The prosthetic valve 100 can further comprise one or more stoppers 112 affixed to the frame 102, such as at an outflow portion 106 of the frame. In the illustrated embodiment, the sleeve 110 is circumferentially aligned with the stopper 112. However, in other embodiments, the sleeve 110 can be circumferentially offset from the stopper 112.

The actuator assemblies 205 can be used to radially expand the prosthetic valve 100 from a radially compressed state to a radially expanded state at an implantation site within a patient's body, as further described below. In some embodiments, the prosthetic valve 100 can further include one or more locking mechanisms (not shown), for example, a locking screw and a proximal nut, that maintain the prosthetic valve in an expanded configuration. After the frame 102 is expanded to a desired radially expanded size, the locking mechanism can be actuated or can self-actuate to lock the frame 102 in the desired radially expanded size. The actuator assemblies 205 can then be released from the prosthetic valve 100 and removed from the body. Further details of the actuator assemblies and the locking mechanism can be found in U.S. Patent Publication 2018/0153689 incorporated herein by reference in its entirety.

Figure 3:
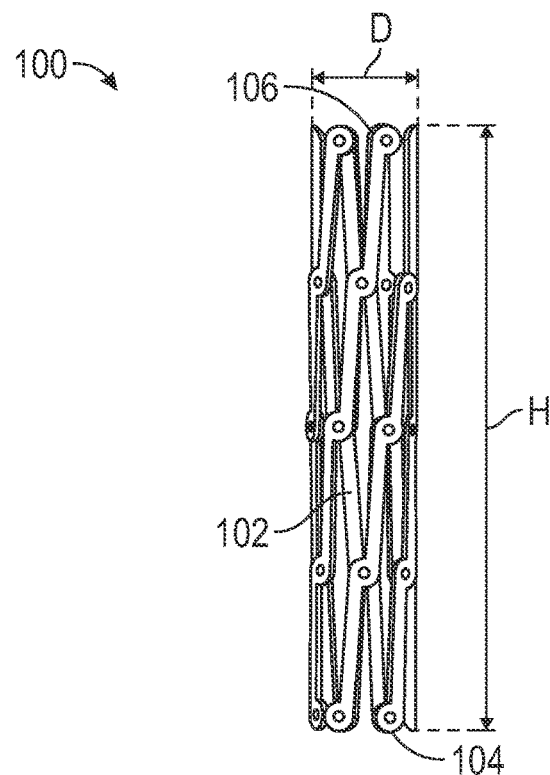
FIG. 3 is a side view of the frame of the prosthetic heart valve of FIG. 2 shown in a radially collapsed configuration.
Figure 4:
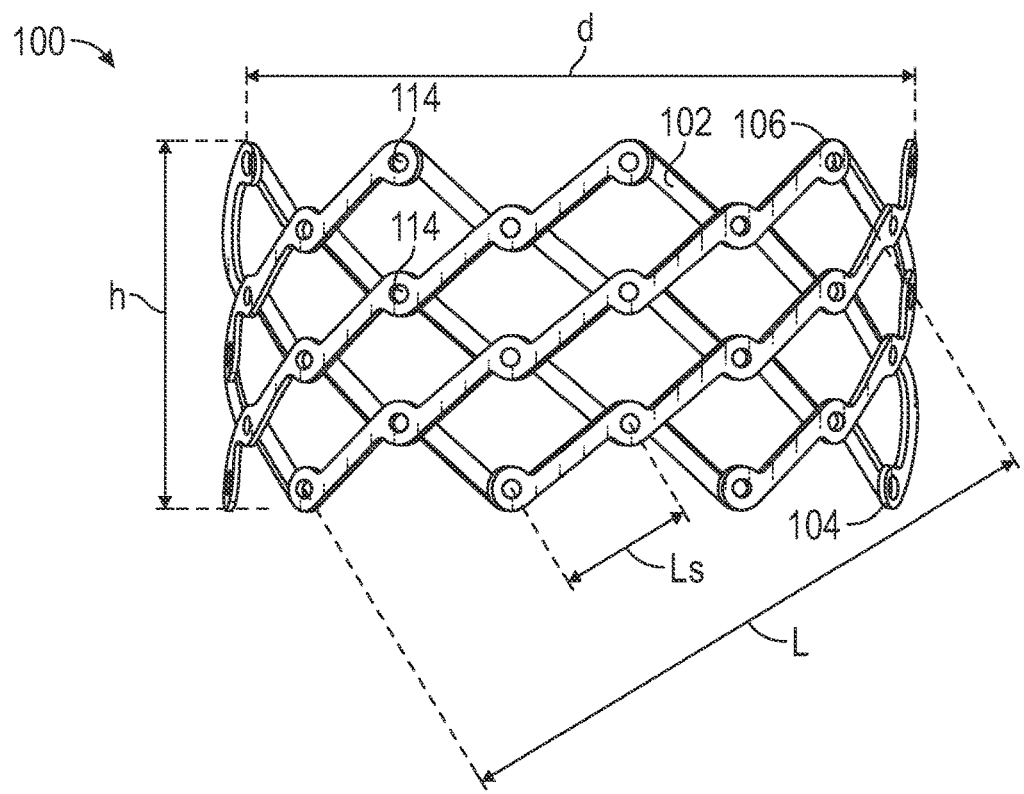
FIG. 4 is a side view of the frame of the prosthetic heart valve of FIG. 2 shown in a radially expanded configuration.

FIGS. 3-4 illustrate the bare frame 102 (without the leaflets and other components) of the prosthetic valve 100 for purposes of illustrating expansion of the prosthetic valve from the radially compressed configuration to the radially expanded configuration. FIG. 3 shows the frame 102 in the radially compressed configuration, and FIG. 4 shows the frame 102 in the fully radially expanded configuration. The prosthetic valve 100 in the illustrated configuration can be radially expanded by maintaining the first end 104 of the frame 102 at a fixed position while applying a force in the axial direction against the second end 106 toward the first end 104. Alternatively, the prosthetic valve 100 can be expanded by applying an axial force against the first end 104 while maintaining the second end 106 at a fixed position, or by applying opposing axial forces to the first and second ends 104, 106, respectively.

Figure 5:
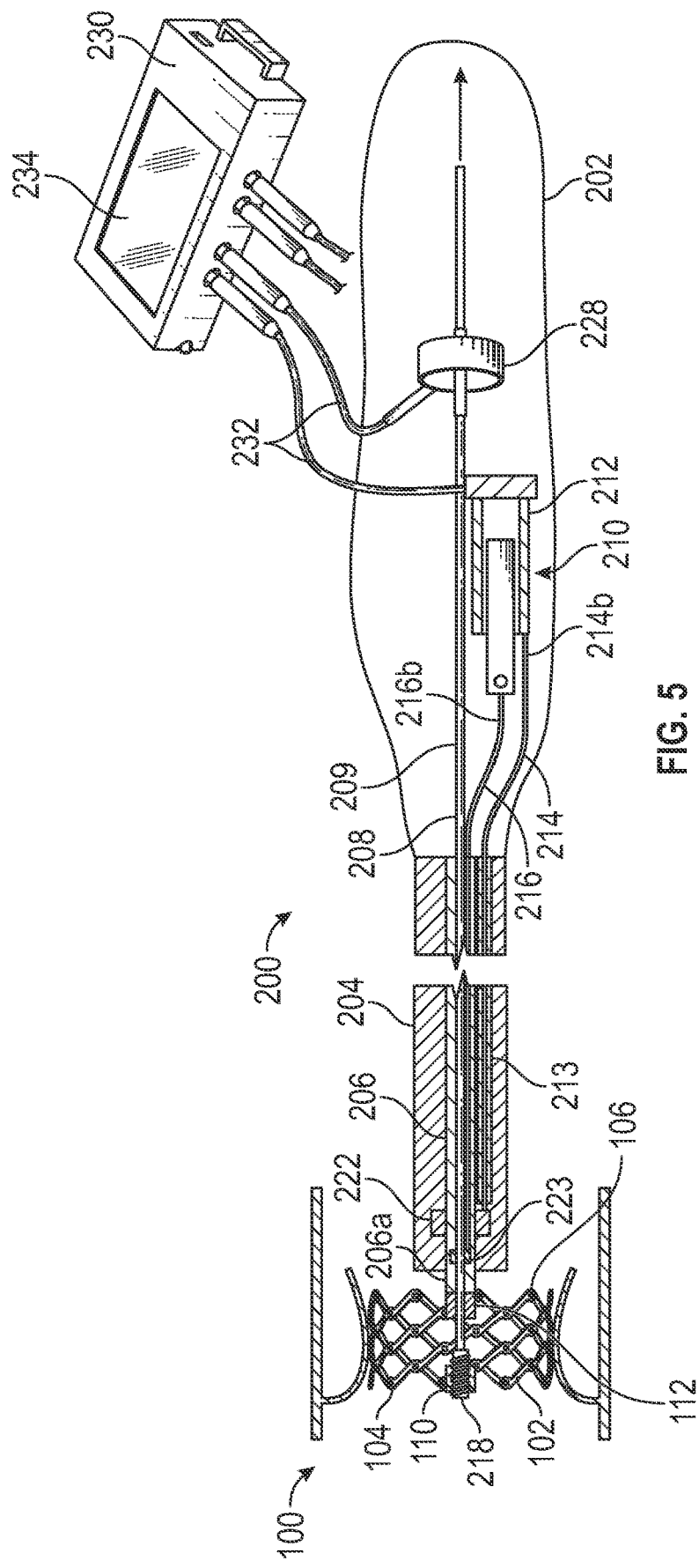
FIG. 5 is an exemplary prosthetic valve delivery apparatus shown being used to implant the prosthetic heart valve of FIG. 2.

FIG. 5 illustrates a delivery apparatus 200, according to one embodiment, adapted to deliver a prosthetic heart valve, such as the illustrated prosthetic heart valve 100, described above. The prosthetic valve 100 can be releasably coupled to the delivery apparatus 200, as further described below. It should be understood that the delivery apparatus 200 and other delivery apparatuses disclosed herein can be used to implant prosthetic devices other than prosthetic valves, such as stents or grafts.

The delivery apparatus 200 in the illustrated embodiment generally includes a handle 202, a first elongated shaft 204 (which comprises an outer shaft in the illustrated embodiment) extending distally from the handle 202, at least one actuator assembly 205 extending distally through the outer shaft 204, and a measurement device 210 for measuring the real-time diameter of the prosthetic valve. The at least one actuator assembly 205 can comprise a first actuator 206 and a second actuator 208. The measurement device 210 can comprise a sensor 212, a first motion-transmitting member 214 coupled to the first actuator 206, and a second motion-transmitting member 216 coupled to the second actuator 208.

In the illustrated embodiment, only one actuator assembly 205 is shown. However, the delivery apparatus 200 can include a plurality of actuator assemblies 205, which can be circumferentially spaced apart from each other and can extend axially through the shaft 204 from the handle 202 to the prosthetic valve 100. Similarly, only one first motion-transmitting member 214 and one second motion-transmitting member 216 is shown in the illustrated embodiment. However, in alternative embodiments, a pair of first and second motion-transmitting members 214, 216 can be provided for each actuator assembly 205 where multiple actuator assemblies 205 are provided.

In the following description, reference is made to a single actuator assembly. However, it should be understood that the description also applies to each actuator assembly where multiple actuator assemblies are present. In the illustrated embodiment, the second actuator 208 extends through the first actuator 206. However, in other embodiments, the first and second actuators 206, 208 may be spaced apart from each other circumferentially around the prosthetic valve 100. The first actuator 206 can be, for example, a sleeve, cylinder, shaft, tube, or other member configured to apply a distally directed forced to the prosthetic valve, such as at the sleeve 112.

The second actuator 208 can comprise an elongated actuator member 209 in the form of, for example, a rod, shaft, cable, wire, suture, or other member configured to apply a proximally directed force to the prosthetic valve, and a screw 218 affixed to the distal end of the member 209. In some embodiments, as shown in FIG. 2, the second actuator 208 can further comprise a cover tube or outer shaft 220 disposed around the actuator member 209 and extending through first actuator 206. The cover tube 220 can annularly surround the actuator member 209 and can be connected to the actuator member 209 such that the actuator member and the cover tube can rotate together and move axially together.

As further shown in FIG. 2, the actuator member 209 and the cover tube 220 can extend through the stopper 112. The screw 218 is configured to be received in and threadably engage internal threads of the nut 110 so as to releasably couple the delivery apparatus 200 to the prosthetic valve (as shown in FIG. 5). The first actuator 206 can annularly surround the cover tube 220. The stopper 112 can have an annular inner surface with an inner diameter larger than the outer diameter of the cover tube 220 and the screw 218 such that the cover tube 220 and the screw 218 can be retracted through the stopper 112 as the frame is expanded and once the delivery apparatus 200 is disconnected from the frame. The stopper 112 is sized to abut or engage the distal end of the first actuator 206 such that the first actuator 206 is prevented from moving distally beyond the stopper. The cover tube 220 facilitates passage of the screw 218 through the stopper 112.

Although the prosthetic valve 100 in the illustrated embodiment is shown as having only one pair of a nut 110 and a corresponding sleeve 112 for coupling with a respective actuator assembly 205 of the delivery apparatus, it should be understood that a pair of a nut 110 and a sleeve 112 can be provided for each actuator assembly. Each pair of a nut 110 and a sleeve 112 can be mounted to the frame at circumferentially spaced apart locations.

In some embodiments, the outer shaft 204 of the delivery apparatus can be configured as a steerable guide catheter having an adjustable curvature for use in steering the delivery apparatus through the patient's vasculature. In particular embodiments, the outer shaft 204 can include a steerable distal section the curvature of which can be adjusted by the operator to assist in guiding the apparatus through the patient's vasculature. A steering or pull wire (not shown) can extend through the outer shaft 204 and can have a distal end fixed at a location along the distal section and a proximal end operatively connected to an adjustment mechanism, for example, a knob on the handle 202. Further details of steering mechanisms that can be incorporated in the delivery apparatus can be found in U.S. Patent Application Publication Nos. 2009/0281619 and 2016/0158497, which are incorporated herein by reference.

In some embodiments, the outer shaft 204 and the actuator assembly 205 can be moved relative to one another (axially and/or rotationally) to facilitate delivery and positioning of the prosthetic valve 100 at an implantation site in the patient's body. The handle 202 can include an adjustment mechanism configured to produce relative movement between the outer shaft 204 and the actuator assembly 205. For example, the handle 202 can include a slidable or rotatable adjustment knob that is operatively connected to the actuator assembly 205 and configured to produce axial movement of the actuator assembly 205 in the proximal and distal directions relative to the outer shaft 204.

In some embodiments, the distal end portion of the outer shaft 204 can form a sheath that is sized and shaped to receive and house the prosthetic valve in a radially compressed state for delivery into and through a patient's vasculature. Once the prosthetic valve is advanced to the implantation site or adjacent the implantation site, the prosthetic valve can be advanced from the sheath by advancing the first and second actuators relative to the shaft 204, after which the prosthetic valve can be radially expanded. In alternative embodiments, the shaft 204 can be configured to move axially relative to the first and second actuators 206, 208, such as by operating a knob on the handle 202. The knob can be operatively connected to the proximal end portion of the shaft 204 and can be configured to retract the shaft 204 proximally relative to the actuators 206, 208 to deploy a prosthetic valve from the distal end of the sheath.

As shown in FIG. 5, a medical assembly can comprise the delivery apparatus 200 and the prosthetic valve 100 coupled to the distal end of the delivery apparatus. When the prosthetic valve 200 is coupled to the delivery apparatus, a distal end portion 206a of the first actuator 206 can abut a corresponding stopper 112 of the frame 102. The stopper 112 is sized to prevent the first actuator 206 from moving distally beyond the stopper 112.

As noted above, the screw 218 of the second actuator 208 can be connected to a corresponding nut 110 on the frame 102 to effectively couple the prosthetic valve to the delivery apparatus. Once the prosthetic valve 100 has been deployed at the desired implantation location, the screw 218 can be removed from the nut 110 to release the prosthetic valve from the delivery apparatus. The stopper 112 can have an annular inner surface with an inner diameter larger than the outer diameter of the actuator member 209, the outer tube 220 and the screw 218 such that the actuator member 209, the outer tube 220 and the screw 218 can be retracted through the stopper 112 as the frame 102 is expanded and once the second actuator 208 is disconnected from the frame by unscrewing the screw 218 from the nut 110.

The first actuator 206 can be configured to apply a distally directed force to the proximal end portion 106 of the prosthetic valve 100. When the screw 218 of the second actuator 208 is connected to the nut 110, the second actuator 208 can be configured to apply a proximally directed force to the distal end portion 104 of the prosthetic valve 100.

The proximal end portion of the actuator member 209 of the second actuator 208 can be operatively connected to a control mechanism, such as a control knob on the handle 202, that allows a doctor or operator of the delivery apparatus 200 to rotate the actuator member 209 (e.g., to unscrew the screw 218 from the nut 110) and/or to move the actuator member 209 axially relative to the first actuator 206 to apply a proximally directed force to the prosthetic valve during valve expansion. Similarly, the proximal end portion of first actuator 206 can be operatively connected to a control mechanism, such as a control knob on the handle 202, that allows a doctor or operator of the delivery apparatus 200 to move the first actuator 206 axially relative to the second actuator 208 to apply a distally directed force to the prosthetic valve during valve expansion. The first and second actuators 206, 208 can apply force separately or in combination to radially expand the prosthetic valve, as further described in U.S. Patent Publication 2018/0153689.

In other embodiments, the delivery apparatus 200 can be used to delivery and implant the prosthetic valve 10 of FIG. 1, as follows. A distal end portion 206a of the first actuator 206 can engage or abut a corresponding outer member 36 and a distal end portion 208a of the second actuator 208 can be coupled to a corresponding inner member 34 (in other words, inner members 42 in FIG. 1 represent actuators 208). In this way, the delivery apparatus can apply a distally directed force to the outer members 36 and/or apply a proximally directed force to the inner members 34 to move the prosthetic valve 10 between the radially compressed and radially expanded configurations.

When implanting a mechanically expandable prosthetic valve (e.g., prosthetic valve 100) it is desirable to expand the prosthetic valve to the maximum size allowed by the patient's anatomical considerations while mitigating the risk of annular rupture (e.g., by selecting a size similar to the native annulus). To ensure optimal implantation size, the diameter of the prosthetic valve and the radial force applied to the annulus by the prosthetic valve can be monitored in real time during the implantation process using a measurement device 210.

Referring again to FIG. 5, in the illustrated embodiment, the sensor 212 is disposed within the handle 202 of delivery apparatus 200. However, in other embodiments, the sensor can be mounted outside of the handle 202 and/or can be removably coupled to the delivery apparatus 200.

Figure 6:
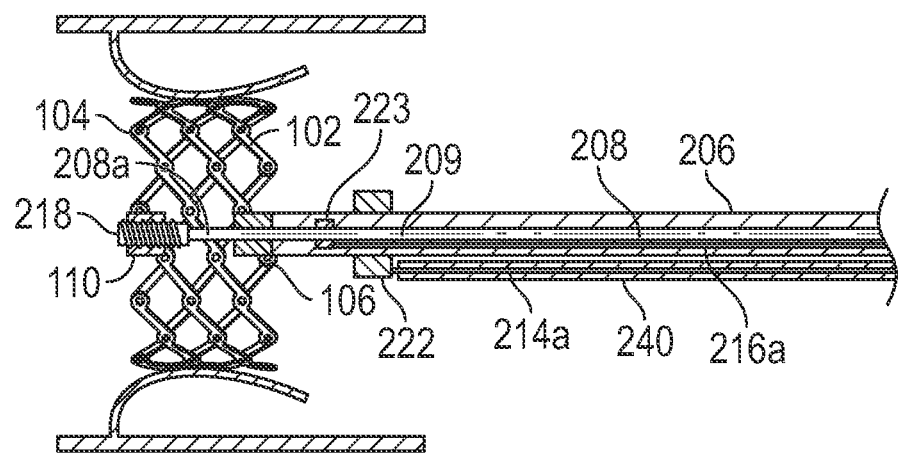
FIG. 6 is an enlarged, partial cross-sectional view of the distal end portion of the delivery apparatus and the prosthetic heart valve of FIG. 5.
Figure 7:
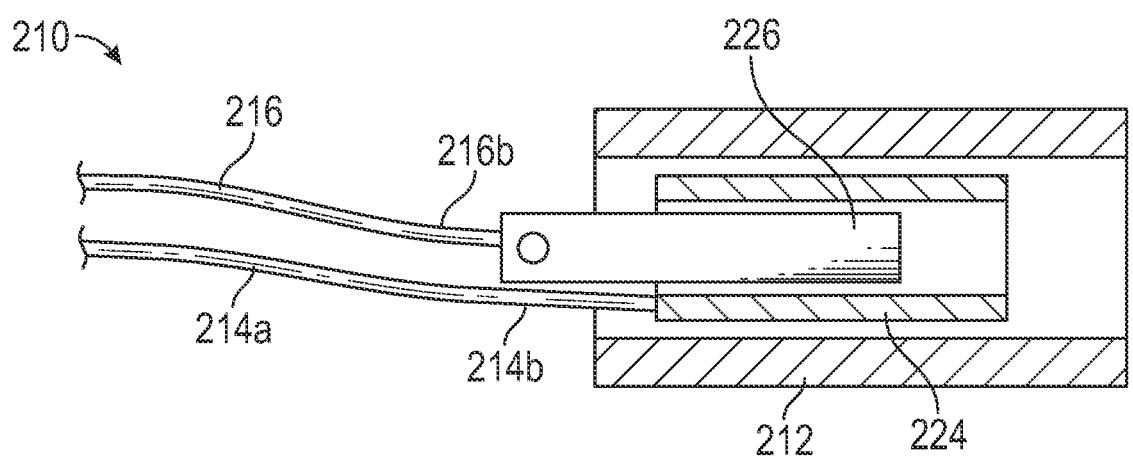
FIG. 7 is a side view of an exemplary sensor used to measure the real-time diameter of a prosthetic heart valve during expansion.

As shown in FIG. 6, the first motion-transmitting member 214 of the measurement device 210 can have a distal end portion 214a coupled to a corresponding first actuator 206 such that axial movement of the first actuator 206 in the proximal and distal directions causes corresponding axial movement of the first motion-transmitting member 214. For example, the distal end portion 214a can be connected to a ring 222 mounted around and affixed to the first actuator 206. In alternative embodiments, other coupling means can be used to the couple the first motion-transmitting member 214 to the first actuator. As best shown in FIG. 7, a proximal end portion 214b of the first motion-transmitting member 214 can be coupled to the sensor 212.

The second motion-transmitting member 216 can have a distal end portion 216a coupled to a corresponding second actuator 208 such that axial movement of the second actuator 208 in the proximal and distal directions causes corresponding axial movement of the second motion-transmitting member 214. For example, the distal end portion 216a can be connected to a ring 223 mounted around and affixed to the actuator member 209 of the second actuator 208 (FIG. 6). In alternative embodiments, other coupling means can be used to couple the second motion-transmitting member 216 to the second actuator 208. A proximal end portion 216b of the second motion-transmitting member can be coupled to the sensor 212 (FIG. 7).

In particular embodiments, the first and second motion-transmitting members 214, 216 extend at least along the majority of the lengths of the first and second actuators 206, 208, and more desirably extend substantially the entire length of the first and second actuators 206, 208. Further, as best shown in FIG. 6, the distal end portions of the first and second motion-transmitting members 214, 216 desirably are coupled to the first and second actuators 206, 208, respectively, at locations adjacent the prosthetic valve 100.

The motion-transmitting members 214, 216 can be, for example, wires, rods, shafts, or other flexible, inelastic members configured to have sufficient rigidity such that the members do not bend, buckle, or stretch or compress axially when a proximal or distal force is applied thereto during normal use. In some embodiments, the motion-transmitting members can be cylindrical in shape. In other embodiments, the motion-transmitting members can have any of various other shapes in cross-section, for example, square, triangular, rectangular, etc. In some embodiments, as shown in FIG. 6, the first motion-transmitting member 214 can be covered by a support tube or shaft 240 that can extend co-axially over the first motion-transmitting member 214. The support tube 240 can be configured to support the first motion-transmitting member 214 and prevent it from buckling during use.

Referring now to FIG. 7, the sensor 212 of the measurement device 210 can be a linear displacement sensor such as a linear variable differential transformer (LVDT), an optical linear encoder, a linear potentiometer, an optical sensor, a capacitive sensor, combinations thereof, or another type of sensor configured to measure the relative movement between the proximal end portions 214b, 216b of the first and second motion-transmitting members 214, 216. An LVDT sensor can generally have three coils (not shown) placed end to end around a tube 224 in which a cylindrical ferromagnetic core 226 is disposed. The tube 224 can be attached to, for example, the proximal end portion 214b of the first motion-transmitting member 214. The core 226 can be attached to, for example, the proximal end portion 216b of the second motion-transmitting member 216. As the prosthetic valve 100 moves between the radially compressed and radially expanded configurations, the core 226 moves relative to the tube 224 creating a voltage differential between the coils which can be converted by the sensor 212 into a relative distance corresponding to the diameter of the prosthetic valve.

For example, during expansion of the prosthetic valve 100, the first actuator 206 can move distally and/or the second actuator 208 can move proximally, thus causing the first motion-transmitting member 214 to move distally relative to the second motion-transmitting member 216 and/or the second motion-transmitting member 214 to move proximally relative to the first motion-transmitting member 216. The sensor 212 measures the relative axial movement $R_1$ of the motion-transmitting members 214, 216, which is a measure of the change in distance or spacing between two points on the motion-transmitting members. The relative movement $R_1$ can be subtracted from the starting height H (see FIG. 3) of the prosthetic valve 100 in its radially compressed configuration in order to calculate the current and/or expanded height h (see FIG. 4) of the prosthetic valve according to the equation:

Equation 1: $h=(H-R_1)$; where h=current/expanded height of the valve; H=crimped height of valve; and $R_1$=relative axial movement between the motion-transmitting members.

The expanded height h of the prosthetic valve 100 can be used to calculate the current diameter d (see FIG. 4) of the prosthetic valve 100 using the following equation:

$$d = \sqrt{L^2 - h^2} \times \frac{18}{5x\pi}; \qquad \text{Equation 2}$$

where d=diameter; L=length of strut (a fixed length); and h=expanded height of valve.

The measurement device 210 can be operatively coupled to a control unit 230 using one or more wires or cables 232 or via a wireless communication link. The control unit 230 can comprise a display 234 and can be configured to receive signals from the sensor 212 representative of the relative axial movement $R_1$ of the first and second motion-transmitting members 214, 216. The control until 230 can be configured to continuously calculate the diameter of the prosthetic valve 100 based on the measurement inputs provided by the sensor 212 and to display the diameter of the prosthetic valve 100 on the display 234 in real-time as the prosthetic valve is expanded during an implantation procedure.

In some embodiments, the control unit 230 can be configured to calculate the real-time diameter of the prosthetic valve using Equations 1 and 2 above. In alternative embodiments, instead of using the equation above, the diameter of the prosthetic valve 100 can be calculated based on pre-programmed data correlating valve diameter to valve height or relative axial movement $R_1$ for a particular prosthetic valve. Thus, for any prosthetic valve that decreases in height as it expands radially, the diameter of the valve can be determined at a plurality of different heights h or distances $R_1$. This data can be stored in memory of the control unit 230, which is programmed to calculate and display the real-time diameter of the prosthetic valve based on the data correlating valve diameter to valve height or distance $R_1$.

During the implantation procedure, a physician can monitor the diameter d of the valve to determine when the prosthetic valve is at the diameter that best fits the native annulus. The implantation procedure and prosthetic valve expansion are explained in more detail below.

As noted above, the first and second motion-transmitting members 214, 216 desirably extend substantially the entire length of the first and second actuators 206, 208 are coupled to first and second actuators 206, 208 adjacent the prosthetic valve. In this manner, movement of the first and second motion-transmitting members 214, 216 accurately reflects movement of the opposing ends of the prosthetic valve. Compression of the first actuator 206, elongation of the second actuator 208, bending of the delivery apparatus, and/or clearance between components of the delivery apparatus have little effect, if any, on axial movement of the first and second motion-transmitting members 214, 216. In other words, the first and second motion-transmitting members 214, 216 isolate the sensor 212 from forces acting on the first and second actuators between the handle and the locations where the motion-transmitting members are connected to the actuators to provide an accurate measurement of the movement of the opposing ends of the prosthetic valve, which in turn yields an accurate measurement of the diameter of the prosthetic valve.

As noted above, the delivery apparatus 200 can include plural actuator assemblies 205. Where plural actuator assemblies 205 are provided, the delivery apparatus can include one measurement device 210 including one set of first and second motion-transmitting members 214, 216 and one sensor 212, in which case the measurement device is used to measure the change in height of the prosthetic valve based on the movements of first and second actuators 206, 208 of one actuator assembly 205. In other embodiments, a measurement device 210, including a set of first and second motion-transmitting members 214, 216 and a sensor 212, can be provided for each actuator assembly 205 and the control unit 230 can receive signals from the sensors 212 and calculate the real-time diameter of the prosthetic valve based on the measurements of each of the sensors.

Referring again to FIG. 5, in some embodiments, the delivery apparatus can further comprise a load cell 228 operatively connected to the proximal end portion of the actuator member 209 of the second actuator 208. The load cell can be housed in the handle as shown. The load cell 228 is configured to measure the tensile force applied by the actuator member 209 on the prosthetic valve. The tensile force can then be used to calculate the radial force applied by the prosthetic valve 100 against the surrounding tissue (e.g., the native annulus) according to the equation:

$$\frac{F_r}{F_a} = \left(4L_s^2 - \frac{4\pi^2}{81}r^2\right)^{-1/2} \times \frac{4\pi^2}{81}r; \qquad \text{Equation 3}$$

wherein $F_r$=radial force output; $F_a$=actuator force; $L_s$=length of a segment of the strut between apertures 114/hinges connecting the struts; a fixed length; and r=radius.

In particular embodiments, the load cell can be an in-line load cell such as, for example, a compression load cell, a strain gauge load cell, a piezoelectric load cell, a pneumatic load cell, and/or a hydraulic load cell.

The load cell 228 can be operatively coupled to the control unit 230 using one or more wires or cables 232 or via a wireless communication link. The control unit 230 can be configured to receive signals from the load cell 228. The control until 230 can be configured to continuously calculate the radial force of the prosthetic valve 100 based on the measurement inputs provided by the load cell 228 and to display the real-time radial force exerted by the prosthetic valve 100 on the display 234 in real-time as the prosthetic valve is expanded during an implantation procedure.

In some embodiments, the control unit 230 can calculate the real-time radial force of the prosthetic valve using Equation 3 above. In alternative embodiments, the radial force can be calculated based on pre-programmed data correlating radial force to tensile force for a particular prosthetic valve from the radially compressed state to the radially expanded state. This data can be stored in the control unit 230, which is programmed to calculate and display the real-time radial force of the prosthetic valve based on the data correlating radial force to tensile force.

If plural actuator members 209 are provided, each actuator member 209 can be operatively connected to the load cell 228. The control unit 230 can receive signals from the load cell 228 can calculate the real-time radial force of the prosthetic valve based on the measured tensile forces on the actuator members 209. In alternative embodiments, each actuator member 209 can be operatively connected to a separate load cell 228. Each load cell 228 can be in communication with the control unit 230, which receives signals from the load cells 228 and calculates the real-time radial force of the prosthetic valve based on measurements from the load cells.

In alternative embodiments, the first actuator 206 can be operatively connected to the load cell 228, which is configured to measure the compressive force applied by the first actuator on the prosthetic valve. The control unit 230 can be used to measure the real-time radial force of the prosthetic valve based on the measured compressive force. If plural actuators 206 are provided, each actuator 206 can be operatively connected to the load cell 228. The control unit 230 can receive signals from the load cell 228 can calculate the real-time radial force of the prosthetic valve based on the measured compressive forces on the actuator members 206. In alternative embodiments, each actuator 206 can be operatively connected to a separate load cell 228. Each load cell 228 can be in communication with the control unit 230, which receives signals from the load cells 228 and calculates the real-time radial force of the prosthetic valve based on measurements from the load cells.

In still alternative embodiments, each actuator 206 and 208 can be operatively connected to the load cell 228 (or separate load cells) and the control unit 230 can be used to measure the real-time radial force of the prosthetic valve based on the measured compressive and tensile forces on the actuators 206, 208.

In some embodiments, the control unit 230 can be configured to provide an alert to the user in the event of over-expansion or over-tensioning of the prosthetic valve 100 within the native annulus. The alert can be an audible alert, a visual alert, a tactile alert, etc.

In some embodiments, the control unit 230 can be further configured to control the first and second actuators 206, 208 and expand and/or contract the prosthetic valve 100 according to a pre-programmed expansion algorithm. In some embodiments, the control unit 230 can log data from the implantation procedure and/or transmit data (e.g., logged data or real-time data) to a remote device.

In some embodiments, the control unit 230 and display 234 can be formed separately from the delivery apparatus 200 and operatively connected thereto, for example, using wires or cables 232. In other embodiments, the control unit 230 can be configured to communicate wirelessly with the sensor 212 and the load cell 228, such as via a Bluetooth connection, radio waves, or infrared signals. In still other embodiments, the control unit 230 and display 234 can be formed integrally with the handle 202. For example, the processor and other electrical components of the control unit 230 can be located within the handle 202 and the display 234 can be located on an exterior surface of the handle 202 such that it can be viewed by a physician during use of the handle 202 in an implantation procedure.

A representative method of implanting the prosthetic heart valve 100 using the delivery apparatus 200 can proceed in the following manner. The prosthetic valve 100 can be connected to delivery apparatus 200 as described above. The distal end portion of the delivery apparatus 200 (along with the prosthetic valve 100) can be advanced through a femoral artery and the aorta toward the native aortic valve.

Once the prosthetic valve 100 is at the desired implantation location, the prosthetic valve can be deployed by, for example, rotating a knob of the handle 202 to advance the prosthetic valve 100 from the sheath of the outer shaft 204. To expand the prosthetic valve, the first actuator 206 can, for example, be advanced distally relative to the handle 202 thus applying a distally directed (e.g., pushing) force to the proximal end portion 106 of the prosthetic valve 100, while the second actuator 208 is simultaneously retracted proximally, thus applying a proximally directed force to a distal end portion 104 of the prosthetic valve 100.

Alternatively, the first actuator 206 can be advanced distally relative to the handle 202, applying a distally directed force to the proximal end portion 106 of the prosthetic valve 100, while the second actuator 208, for example, can be held stationary relative to the handle to restrain the distal end portion 104 of the frame 102 against movement relative to the handle 202.

Still alternatively, the first actuator 206 can be held stationary relative to the handle to restrain the proximal end portion 106 of the frame 102 against movement relative to the handle 202, while the second actuator 208 is retracted proximally applying a proximally directed (e.g., pulling) force to a distal end portion 104 of the prosthetic valve 100.

Application of proximally and/or distally applied forces to the proximal and distal end portions 106, 104 of the prosthetic valve 100 causes the struts 116 of the frame 102 to pivot relative to one another about the pivot joints at the pivot members 118, causing the prosthetic valve 100 to expand from a radially compressed configuration to a radially expanded configuration. As the struts 116 pivot, the first actuator 206 and the second actuator 208 move relative to one another, causing the distal ends of the first and second motion-transmitting members 214, 216 to move relative to one another. As the frame 102 expands, the second actuator 208 exerts strain on the load cell 228. The control unit 230 can then calculate the current diameter and the radial force of the prosthetic valve 100 continuously as it expands and display the values on the display 234.

Access to continuous real-time diameter monitoring allows a physician to implant the prosthetic valve at the optimal diameter to accommodate a specific patient's anatomical variability (e.g., selecting the diameter that is closest in size to the native annulus in which the prosthetic valve is to be implanted). If needed, conventional techniques and/or devices can be used to measure the size of the native heart valve annulus in which the prosthetic heart valve will be implanted. Once the size of the native annulus has been determined, the physician can select a corresponding diameter for the prosthetic valve 100 and use the delivery apparatus 200 to expand the prosthetic valve 100 to the selected diameter. During expansion of the prosthetic valve 100, continuous real-time monitoring of the current diameter and radial force output can help prevent over-expansion, thus mitigating the risk of annular rupture.

The physician can continue to adjust (e.g., by expanding or contracting) the diameter of the prosthetic valve as necessary until the prosthetic valve 100 is expanded to a diameter that best fits the native annulus. For example, prosthetic valve 100 desirably is expanded to a diameter sufficient to anchor the prosthetic valve in place against the surrounding tissue with minimal or no paravalvular leakage and without over-expanding and rupturing the native annulus.

In alternative embodiments, in lieu of the motion-transmitting members, the sensor 212 can be directly coupled to the proximal end portions of the first and second actuators 206, 208. In such embodiments, application of proximally and/or distally applied forces to the proximal and distal end portions 106, 104 of the prosthetic valve 100 causes the prosthetic valve 100 to expand from a radially compressed configuration to a radially expanded configuration and causes the first actuator 206 and the second actuator 208 move relative to one another. Movement of the first and second actuators 206, 208 causes the proximal end portions of the first and second actuators 206, 208 to move relative to one another within the sensor 212 and/or move components of the sensor 212 relative each other. For example, the proximal end portion of the first actuator 206 can be connected directly to the tube 224 and the proximal end portion of the second actuator 208 can be connected directly to the core 226 so that relative movement of the actuators causes corresponding relative movement of the core 226 and the tube 224. The sensor 212 measures the relative axial movement of the first and second actuators 206, 208. The control unit 230 can then calculate the current diameter of the prosthetic valve 100 continuously as it expands and display the values on the display 234.

Figure 8:
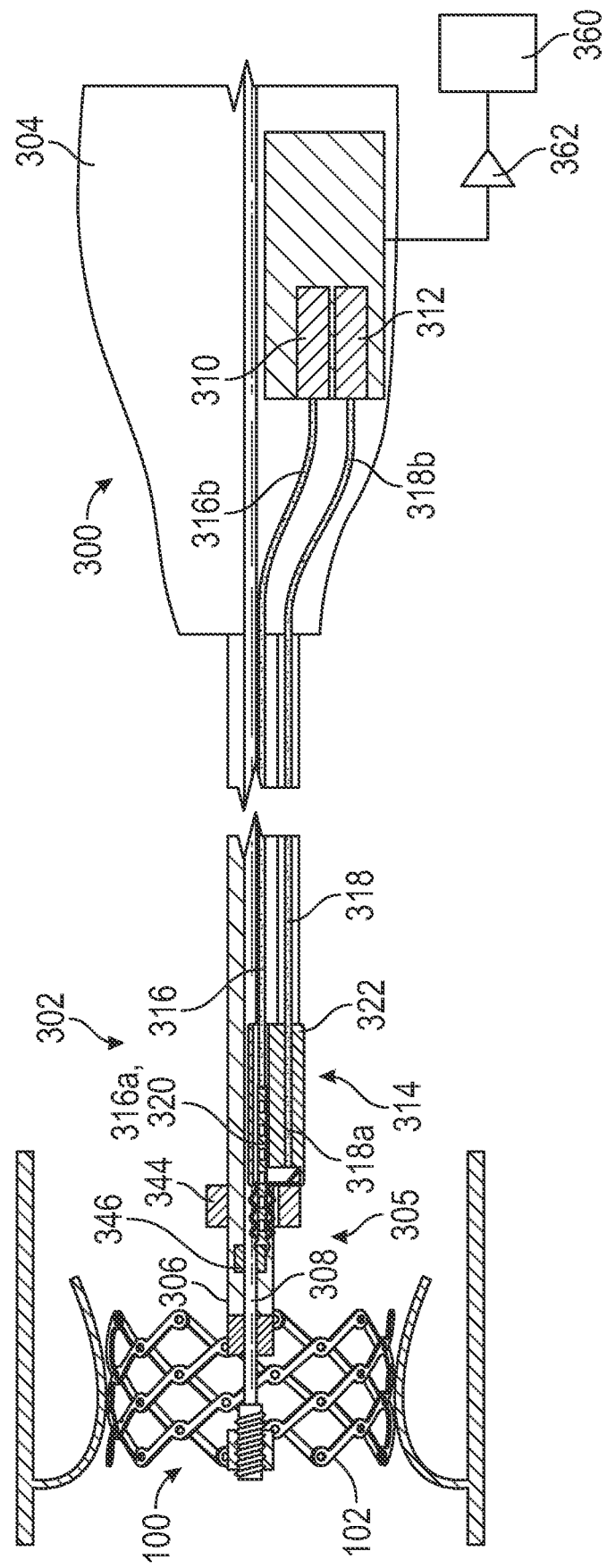
FIG. 8 is a partial cross-sectional view of a distal end portion of another exemplary embodiment of a delivery apparatus being used to implant the prosthetic heart valve of FIG. 2.

FIGS. 8-10 illustrate an exemplary embodiment of a delivery apparatus 300 comprising a measurement device 302. Delivery apparatus 300 can be similar to delivery apparatus 200 described above, and can comprise a handle 304 and one or more actuator assemblies 305 extending distally from the handle 304. Each actuator assembly can comprise a first actuator 306 and a second actuator 308. First actuator 306 can be configured to be releasably coupled to a prosthetic valve 100 at a first location (e.g., to a proximal end portion of the prosthetic valve) and second actuator 308 can be configured to be releasably coupled to the prosthetic valve at a second location (e.g., to a distal end portion of the prosthetic valve). The measurement device 302 can be used to measure the real-time diameter of the prosthetic valve 100 as the prosthetic valve is radially expanded and/or radially compressed.

Referring to FIG. 8, the measurement device 302 can generally comprise a light source or emitter 310, a receiving element 312, and a sensor 314 coupled to the light source and receiver via first and second waveguides, such as optical fibers 316, 318, respectively. Fibers 316 and 318 can each comprise a core and a cladding, and can optionally comprise a protective coating. The fibers 316, 318 can be configured to transmit or propagate optical radiation (e.g., light) along the length of the fiber.

As used herein, "optical radiation" refers to electromagnetic radiation at wavelengths of between about 100 nm and 10 μm, and typically between about 500 nm and 2 μm. Examples based on available laser diode sources and optical fibers generally are associated with wavelengths of between about 800 nm and 1700 nm. In some examples, propagating optical radiation is referred to as one or more beams having diameters, asymmetric fast and slow axes, beam cross-sectional areas, and beam divergences that can depend on beam wavelength and the optical systems used for beam shaping. For convenience, optical radiation is referred to as light in some examples, and need not be at visible wavelengths.

Representative embodiments are described with reference to optical fibers 316, 318, but other types of optical waveguides can be used having square, rectangular, polygonal, oval, elliptical or other cross-sections. Optical fibers are typically formed of silica (glass) that is doped (or undoped) so as to provide predetermined refractive indices or refractive index differences. In some, examples, fibers or other waveguides are made of other materials such as fluorozirconates, fluoroaluminates, fluoride or phosphate glasses, chalcogenide glasses, or crystalline materials such as sapphire, depending on wavelengths of interest. In still other examples, optical fibers can be formed in part of plastics. In typical examples, a doped waveguide core such as a fiber core provides optical gain in response to pumping, and core and claddings are approximately concentric. In other examples, one or more of the core and claddings are decentered, and in some examples, core and cladding orientation and/or displacement vary along the length of the fiber.

The light source 310 can be configured to produce a beam of light and couple the light into the first fiber 316. The light source 310 can be, for example, a light emitting diode (LED), a photodiode array, a laser diode, and/or an incandescent bulb, etc. The receiving element 312 can be configured to receive optical radiation or light propagating through the second fiber 318 and can be, for example, a photoelectric circuit. The light can comprise, for example, one or more lights, such as a pattern of light. In some embodiments, the signal can comprise one or more wavelengths of light.

Generally, light emitted by the light source 310 propagates through the first fiber 316 to the sensor 314. A distal end portion 316a of the first fiber 316 can be configured to emit light. The emitted light is re-directed into the second fiber 318 and transmitted through the second fiber 318 to the receiving element 312, as described in more detail below.

In the illustrated embodiment, the light source 310 and receiving element 312 are disposed in the handle 304 of the delivery apparatus 300, and the sensor 314 is disposed along a distal end portion of the delivery apparatus 300, adjacent the prosthetic valve 100. The small distance between the prosthetic valve 100 and the sensor 314 can prevent or mitigate measurement error caused by factors such as compression of the delivery device and/or elongation of the actuation mechanism under tension. However, in other embodiments, the light source 310, receiving element 312, and sensor 314 can all be disposed within the handle 304 or at some other location on the delivery apparatus that remains outside of the patient's body during use. In such embodiments, the portion of the first fiber 316 configured to emit light can likewise be disposed in the handle 304.

In the illustrated embodiment, only one actuator assembly 305 comprising first actuator 306 and second actuator 308 is shown. However, the delivery apparatus 300 can include a plurality of actuator assemblies 305, which can be circumferentially spaced apart from each other and can extend axially through an outer shaft (such as outer shaft 204 of FIG. 5) from the handle 304 to the prosthetic valve 100. Similarly, only one first fiber 316 and one second fiber 318 are shown in the illustrated embodiment. However, in alternative embodiments, a pair of first and second fibers 316, 318 can be provided for each actuator assembly 305 where multiple actuator assemblies 305 are provided.

Referring now to FIG. 9, the sensor 314 can comprise a housing 322 having a proximal end portion 324 and a distal end portion 326. The housing 322 can include a buffer member 328 defining an inner lumen 330 into which a distal end portion 318a of the second fiber 318 can extend. The buffer member 328 can extend axially at least partially along the length of the housing 322. A recess 332 is defined within the housing 322. In the illustrated embodiment, the recess 332 is disposed along the distal end portion 326 of the housing 322 between the distal end of the buffer member 328 and a distal wall of the housing. However, in other embodiments, the recess can be positioned at any location along the length of the housing 322. An optical coupler 334 can be positioned within the recess 332 and can be configured to couple light emitted by the distal end portion 316a of the first fiber 316 into the distal end face 336 of the second fiber 318, as represented by arrows 338 (FIG. 10).

For example, in the illustrated embodiment, the optical coupler 334 can comprise a reflective element (e.g., a mirror) positioned at an approximately 45-degree angle relative to an internal surface 340 of the housing. However, in other embodiments, the optical coupler can be, for example, a 45-45-90 prism with a flat hypotenuse surface comprising a reflective metal. In some embodiments, the hypotenuse surface can be curved to provide additional focusing or optical power.

In still other embodiments, the optical coupler 334 can be a cut or otherwise modified portion of the second fiber 318. In some embodiments, the distal end face 336 of the second fiber 318 can be cut such that it extends at an angle relative to an internal surface of the housing 334. In such embodiments, the distal end face 336 of the second fiber 318 can extend past a distal edge 342 of the buffer member 328 and into the recess 332. In some embodiments, the distal tip portion of the second fiber 318 can be bent toward the side surface of the first fiber 316, for example, at a 90-degree angle so that the end face 336 faces the side of the first fiber 316 within the recess 332, in which case the coupler 334 can be optional.

The buffer member 328 can comprise an opaque or light-resistant material configured to prevent light emitted by the first fiber 316 from entering the second fiber 318 except at the exposed distal end face 336.

Referring again to FIG. 8, the housing 322 of the sensor 314 can be coupled to the first actuator 306. In the illustrated embodiment, the housing 322 extends radially through a wall of the first actuator 306 such that a portion of the housing 322 is disposed within a lumen of the first actuator 306 and a portion of the housing 322 is disposed within the wall of the first actuator 306. The housing 322 can be fixed in place relative to the first actuator 306 using a ring 344 mounted around and affixed to the first actuator 306 and affixed to the housing 322. In other embodiments, the housing 322 of the sensor 314 can be fully contained within the wall of the first actuator 306. In still other embodiments, the housing 322 can be coupled to an outer surface of the first actuator 306.

The first fiber 316 can extend through the housing 322 and can be axially movable relative to the housing 322. The first fiber 316 can have a distal end portion 316a and a proximal end portion 316b. The distal end portion 316a can be coupled to the second actuator 308 of the delivery apparatus 300 at a location adjacent the prosthetic valve 100. Movement of the second actuator 308 (e.g., during radial expansion of the prosthetic valve 100) can result in corresponding movement of the first fiber 316. For example, a tip portion 315 of the first fiber 316 can be connected to a ring 346 mounted around and affixed to the second actuator 308. In alternative embodiments, other coupling means (e.g., adhesives, etc.) can be used to couple the first fiber 316 to the second actuator 308. The proximal end portion 316b of the first fiber can be coupled to the light source 310.

The second fiber 318 can have a distal end portion 318a and a proximal end portion 318b. The distal end portion 318a can extend into the lumen 330 of the buffer member 328 and can be fixed relative to the housing 322 using, for example, an adhesive. As best seen in FIG. 9, the second fiber 318 can be fixed relative to the buffer member 328 such that a distal end face 336 of the second fiber 318 aligns or substantially aligns with a distal edge 342 of the buffer member 328. In embodiments wherein the coupling element 334 comprises a cut or otherwise modified portion of the second fiber 318, the distal end portion 318a of the second fiber 318 can extend past the distal edge 342 and into the recess 332. As best seen in FIG. 8, the proximal end portion 318b of the second fiber 318 can be coupled to the receiving element 312.

Referring again to FIG. 9, the distal end portion 316a of the first fiber 316 can be configured such that relative axial movement between the first fiber 316 and the housing 322 (and the second fiber 318) produces a light pattern that is representative of radial expansion or compression of the prosthetic valve. The light pattern is transmitted to the receiving element 312 via the second fiber 318. The control unit 360 can be programmed to determine the diameter of the prosthetic valve as the prosthetic valve is radially expanded and/or compressed within the patient's body based on light pattern sensed by the receiving element 312. This can be accomplished, for example, by providing, along the length of the distal end portion 316a, sections of varying transmissivity of light in a lateral or radial direction and/or sections that can emit selected wavelengths of light in a lateral or radial direction. In the present disclosure, light traveling in a "lateral" direction means that light is emitted from the outer side surface of the fiber 316.

In the illustrated embodiment of FIGS. 9-10, for example, the distal end portion 316a has a pattern of first sections 348 alternating with second sections 350 along the length of the distal end portion 316a. First sections 348 (also referred to as marked portions in some embodiments) prevent or minimize the amount of light that is emitted from the first fiber 316 in a radial or lateral direction into the housing 322. Second sections 350 allow light (or more light than allowed by first sections 348) to be emitted into the recess 332 of the housing 322. Thus, as the first fiber 316 is moved longitudinally, relative to the housing 322, the first fiber produces a light pattern comprised of flashes of light alternating with no light (or flashes of less light) into the recess 332, which is then reflected into the second fiber 318 and transmitted to the receiving element 312. The light pattern can then be used to determine the diameter of the prosthetic valve, as further described below.

The sections of varying transmissivity can be formed in a variety of ways. In the illustrated embodiment, the distal end portion 316 can comprise a bare fiber core (e.g., a glass core) that is surrounded by a diffusing element or layer 320 (e.g., one or more light-transmitting polymer layers) that has a higher index of refraction that the fiber core to facilitate the emission of light in a lateral direction from the fiber core. First sections 348 can be opaque sections formed on the diffusing layer 320, such as by painting or otherwise coating the diffusing layer with an opaque material at selected intervals. Second sections 350 can be non-coated or exposed portions of the diffusing layer 320 that allows light to be emitted in a lateral direction into the housing.

In alternative embodiments, the distal end portion 316a can comprise a bare fiber core (e.g., a glass core) without any cladding that is treated at selected intervals to form first and second sections 348, 350. Typically, the core of an optical fiber has a smooth outer surface that prevents all or most of the light from escaping from the core in a lateral direction. Thus, the first sections 348 can be untreated sections of the fiber core having a smooth outer surface. In some embodiments, an opaque material can be applied (e.g., painted) on the fiber core along sections 348 to prevent all light from escaping from the fiber core along those sections. The second sections 350 can be sections of the fiber core that are roughened (e.g., abraded) or otherwise modified to facilitate the emission of light from the fiber core in a lateral direction. For example, any fiber cladding layers can be removed to expose the surface of the fiber core, which can be physically or chemically abraded at selected intervals to form sections 350. The roughened surfaces 350 allow light to diffuse outwardly from the fiber core. In another example, in lieu of or in addition to roughening the surface of the fiber core, the second sections 350 can include notches cut or otherwise formed along those sections of the fiber core which promote the transmission of light from the fiber core in a lateral direction. In another example, the second sections can include a plurality of optical structures or inclusions (e.g., optical nanostructures) within the fiber core. The optical structures can modify the refractive index of the fiber core, allowing light to scatter or leak from the fiber. In some embodiments, the fiber core can additionally be coated with a layer of light diffusing material, such as a light transmitting polymer material, at least along the roughened or notched portions 350.

In other embodiments, in lieu of or in addition to the diffusing element or layer, the distal end portion 316a can comprise a plurality of grooves laser-cut into the cladding surrounding the fiber core to promote diffusion of light in a lateral direction. For example, in particular embodiments, spiral-shaped grooves can be carved into the fiber cladding using lasers (e.g., $CO_2$ lasers). The fiber core can be, for example, a step-index multi-mode fiber having a numerical aperture of 0.22 or 0.37 and a fiber core diameter of >200 µm. The first sections 348 can include opaque layers to prevent diffusion and the second sections 350 can be sections of the grooved fiber that do not have opaque layers. Alternatively, the first second sections 348, 350 can be formed by selectively forming the grooves only along second sections 350, while the first sections 348 include the cladding without any grooves.

In alternative embodiments, the distal end portion 316a can comprise an optical fiber with the cladding removed to expose the bare fiber core at selected intervals to form the second sections 350. The first sections 348 can be sections of the optical fiber that still have the cladding. The second sections 350 can be roughened or formed with notches or inclusions as described above and/or can include one or more diffusing layers formed around the bare fiber core. In such cases, the entire length of the fiber core along the distal end portion 316a can be roughened or formed with notches or inclusions as described above and the distal end portion 316a can include sections of cladding and/or opaque layers at selected intervals to form first sections 348, thereby allowing diffusion at sections 350.

In alternative embodiments, the distal end portion 316a can comprises a bare fiber core that includes sections that are treated to have varying degrees of roughness, and therefore varying degrees of transmissivity in the lateral direction. For example, the first and second sections 348, 350 can be sections of the fiber core that are roughened (e.g., abraded) with the first sections 348 having a relatively less surface roughening than sections 350. This will produce a light pattern comprised of alternating flashes of relatively bright light and relatively dim light.

In any embodiments described herein, the first fiber 316 can comprise a fluorescent optical fiber or rod that naturally emits light in all directions (laterally and longitudinally), as compared to an optical fiber used in telecommunications or other applications wherein the emission of light in the lateral direction is undesirable. A fluorescent optical fiber (sometimes referred to as a "side glow" fiber") can comprise, for example, one or more polymeric layers containing fluorescent particles or dyes. In such embodiments, the second sections 350 can be untreated sections of a bare fiber while the first sections 348 can be formed by applying an opaque material at selected intervals on the bare fiber. However, any of the features and techniques for forming the distal end portion 316a described above can be applied to embodiments where the first fiber comprises a fluorescent optical fiber.

As noted above, the embodiment of FIGS. 9-10 includes a diffusing layer 320 with first sections 348 that are "marked" portions of the layer 320 and second sections 350 that are "exposed" portions of the layer 320. Thus, in the sections that follow that describe the operation of the measurement device 302, sections 348, 350 are referred to as marked portions 348 and exposed portions 350, but it should be understood that the following description applies to embodiments that do not have a diffusing layer but still have sections 348, 350 of varying transmissivity.

The marked portions 348 and exposed portions 350 can have predetermined lengths. Accordingly, the displacement or relative axial movement of the first fiber 316 relative to the housing 322, and therefore the diameter of the prosthetic valve, can be determined by counting the number of marked and/or exposed portions 348, 350 that align with a predetermined location on the housing, for example, the recess 332. As used herein, "aligns" means that at least a portion of a marked and/or exposed portion 348, 350 extends over the recess 332. One or more portions can be aligned with the recess simultaneously, as shown in FIG. 10. When two portions are both aligned with the recess, both portions can affect the light emitted by the first fiber 316. For example, if a marked portion 348 and an exposed portion 350 are both aligned with the recess 332, the light emitted by the exposed portion 350 will be dimmer than if only the exposed portion 350 were aligned with the recess. The control unit 360 can be configured to filter out the dimmer lights and count only each full "flash" or "blink" of light that is generated when only the exposed portion is aligned over the recess. In other words, in some embodiments, the control unit 360 counts the number of times that a portion 350 is fully exposed to the recess while ignoring the times that a portion 350 is only partially exposed to the recess based on the brightness of light.

In some embodiments, the control unit 360 can be configured to determine the extent that an exposed portion 350 extends partially over the recess 332 based on the amount of light detected by the receiving element as compared to the amount of light for a full "flash." If an exposed portion 350 extends partially over the recess, the control unit 360 can determine the length of a portion 350 that is aligned with the recess based on the brightness of the light received by the receiving element 312. In this way, the control unit 360 can calculate the full length of movement of the first fiber 316 relative to the housing 322, and therefore the diameter of the prosthetic valve at any point in time.

Generally, as the prosthetic valve 100 is expanded, the second actuator 308 (and therefore the first fiber 316) moves axially, for example, in a proximal direction. As the first fiber 316 moves, the marked portions 348 of the distal end portion 316a move relative to the housing 322 and align with the recess 332, creating a pattern of emitted light that can be transmitted through the second fiber 318 and received by the receiving element 312, as described in more detail below.

As mentioned previously, the first fiber 316 can extend through the housing 322 and past a distal end portion 326 of the housing 322. The first fiber 316 can extend through an opening 352 in the distal end portion 326. The sensor 314 can further comprise a sealing member 354 configured to extend over the distal end portion 316a of the first fiber 316 and prevent bodily fluids (e.g., blood) from entering the housing 322 through the opening 352. In the illustrated embodiment, the sealing member 354 comprises a bellows seal connected at one end to the distal end portion 326 of the housing and at another end to the tip portion 315 of the first fiber 316. The sealing member defines a lumen 356 into which the distal end portion 316a of the first fiber extends. The sealing member can be formed from a flexible polymeric sheet. The sealing member 354 can be configured to stretch and collapse axially as the first fiber 316 moves distally and proximally, respectively. In an alternative embodiment, the sealing member 354 can be an O-ring disposed around the opening 352. In such embodiments, the O-ring can be sized to fit tightly against the outer surface of the first fiber 316 such that bodily fluids are wiped off the first fiber as it enters the housing 322. In this way, the O-ring prevents or mitigates the entrance of bodily fluids into the housing 322.

Measurement device 302 can comprise a control unit 360 comprising a display. Control unit 360 can be similar to the above-described control unit 230 comprising display 234. The control unit 360 can be operatively coupled to the light source 310 and/or the receiving element 312 via one or more wires or cables and/or via a wireless communication link. The control until 360 can be configured to continuously calculate the diameter of the prosthetic valve 100 based on the measurement inputs provided by the sensor 314 and to display the diameter of the prosthetic valve 100 on the display in real-time as the prosthetic valve 100 is expanded during an implantation procedure. During the implantation procedure, a physician can monitor the diameter d of the valve to determine when the prosthetic valve is at the diameter that best fits the patient's native annulus. In some embodiments, signals from the receiving element 312 and/or light source 310 can be converted from a digital signal to an analog signal using a digital-to-analog converter (DAC) 362.

Referring to FIGS. 9-10, during expansion of the prosthetic valve 100, the first actuator 306 can move distally and/or the second actuator 308 can move proximally, thus causing the first fiber 316 to move axially relative to the sensor 314. When the first fiber 316 is in a first axial position (see e.g., FIG. 9) a marked portion 348a can be aligned with the recess 332. The marked portion 348a prevents or mitigates light from propagating into the recess 332. Accordingly, no light or a minimal amount of light travels through the second fiber 318 to the receiving element 312. As the second actuator 308 moves, the first fiber 316 moves axially to a second axial position (see e.g., FIG. 10). In the second position, an exposed portion 350a can be aligned with the recess 332. Light emitted by the exposed portion 350a can propagate into the recess 332 and be coupled into the end face 336 of the second fiber 318 by the optical coupler 334, as shown by arrows 338. The light can travel through the second fiber 18 and be received by the receiving element 312. In some embodiments, the end face 336 can be roughened and/or formed with notches or other surface features to promote the coupling of light into the second fiber 318.

As the first fiber 316 continues to move axially (e.g., in a proximal direction as shown by arrow 358), alternating marked portions 348 and exposed portions 350 will respectively align with the recess 332 thereby creating "flashes" or "blinks" of light which are transmitted to the receiving element 312. The receiving element 312 can detect the blinks and the control unit 230 can use the number of blinks to calculate the current diameter of the prosthetic valve 100.

As mentioned previously, each marked portion 348 and each exposed portion 350 can have a predetermined length. For example, each marked portion 348 can have a first length $L_1$ and each exposed portion can have a second length $L_2$. In some embodiments, $L_1$ and $L_2$ can be equal. In other embodiments, $L_1$ can be greater than $L_2$ or vice versa. The receiving element 312 can determine the relative axial movement $R_2$ between the first fiber 316 and the sensor 314 by counting the number of blinks. For example, in some particular embodiments, the relative movement $R_2$ can be calculated according to the equation:

Equation 4: $R_2 = n(L_1 + L_2)$; where $R_2$=relative axial movement between the first fiber and the sensor; n=number of blinks; $L_1$=length of each marked portion; and $L_2$=length of each exposed portion.

The relative movement $R_2$ can be subtracted from the starting height H of the prosthetic valve 100 (see e.g., FIG. 3) in its radially compressed configuration in order to calculate the current and/or expanded height h (see e.g., FIG. 4) of the prosthetic valve 100 according to the following equation:

Equation 5: $h = (H - R_2)$; where h=current/expanded height of the valve; H=crimped height of valve; and $R_2$=relative axial movement between the first fiber and the sensor.

The expanded height h can be used to calculate the current diameter d (see e.g., FIG. 4) of the prosthetic valve 100 using Equation 2 described above.

As shown in FIG. 8, the first and second fibers 316, 318 desirably extend substantially the entire length of the first and second actuators 306, 308 and are coupled to first and second actuators 306, 308 at a location adjacent the prosthetic valve 100. Accordingly, movement of the first fiber 316 relative to the sensor 314 accurately reflects the relative movement of the opposing ends of the prosthetic valve 100. Compression of the first actuator 306, elongation of the second actuator 308, bending of the delivery apparatus 300, and/or clearance between components of the delivery apparatus have little effect, if any, on relative movement between the first fiber 316 and the sensor 314. In other words, placement of the sensor 314 adjacent the prosthetic valve 100 (which allows the actual measurement to take place adjacent the prosthetic valve) isolates the sensor 314 and the first fiber 316 from forces acting on the first and second actuators 306, 308 between the handle 304 to provide an accurate measurement of the movement of the opposing ends of the prosthetic valve, which in turn yields an accurate measurement of the diameter of the prosthetic valve.

During implantation, the physician can select a diameter for the prosthetic valve 100 and use the delivery apparatus 300 to expand the prosthetic valve 100 to the selected diameter. During expansion of the prosthetic valve 100, continuous real-time monitoring of the current diameter and radial force output can help prevent over-expansion, thus mitigating the risk of annular rupture.

For example, a user can actuate the handle 304 of the delivery apparatus 300 to move the second actuator 308 proximally and/or to move the first actuator 306 distally. Because the first and second actuators 306, 308 are secured to the frame at axially spaced locations, moving the first and second actuators 306, 308 relative to one anther causes radial expansion or compression of the frame 102. For example, moving the second actuator 308 proximally toward the outflow end of the frame, while holding the first actuator 306 in a fixed position or moving the first actuator distally toward the inflow end of the frame can cause the frame to foreshorten axially and expand radially. As the second actuator 308 moves proximally, the first fiber 316 also moves proximally, resulting in movement of the distal end portion 316a of the first fiber 316 relative to the recess 332. Light transmitted through the first fiber 316 is emitted into the recess 332 in a pattern determined by the marked and exposed portions 348, 350 of the distal end portion 316a. The pattern of emitted light is coupled in to the second fiber 318 by the optical coupler 334 and transmitted to the receiving element 312. The control unit 230 can then use the pattern to continuously calculate the diameter of the prosthetic valve as the prosthetic valve is radially expanded.

FIGS. 11-12 illustrate another exemplary embodiment of a sensor 400 useable with the delivery apparatus 300 and the measurement device 302. The sensor 400 can be used in lieu of or in addition to sensor 314. The sensor 400 can be configured to determine relative movement of a first fiber 401 and the direction of movement (e.g., proximal or distal) of the first fiber 401. Similar to sensor 314, sensor 400 can comprise a housing 402, a buffer member 404 defining a recess 406, and an optical coupler 408. However, the distal end portion 401a of the first fiber 401 comprises marked portions 412, first filtered portions 414, and second filtered portions 416. As light is emitted from the first fiber 401, the pattern produced by the marked portions 412 and the first and second filtered portions 414, 416 allows the receiving element 312 to determine in what direction (e.g., proximally or distally) the first fiber 401 is moving relative to the housing 402. The receiving element 312 can then take the direction of movement into account when calculating the current diameter of the prosthetic valve 100.

As shown in FIG. 11, the distal end portion 401a of the first fiber 401 can comprise a selected pattern of marked and/or filtered portions, 412, 414, 416. For purposes of illustration, the marked portions 412 and the first and second filtered portions 414, 416 include different fill patterns. The marked portions 412 can be configured to prevent or minimize the diffusion of light therethrough. In the illustrated embodiment, the distal end portion 401a of the first fiber comprises a bare fiber core and a diffusing layer 410 extending over the bare fiber core. The marked portions 412 can be formed on the diffusing layer 410. In other embodiments, the marked portions 412 can be formed directly on the bare fiber core of the first fiber 401. The marked portions 412 can be, for example, opaque masks comprising a coating, a paint, etc.

In other embodiments, the marked portions 412 do not necessarily need to be layers of material formed on the diffusing layer or on the bare fiber core. Instead, as described above, these portions can simply be untreated sections of the bare fiber core or sections of the optical fiber that have a cladding. Thus, in certain embodiments, portions 412 can simply be referred to as sections of the first fiber that do not emit light in the lateral direction, or less light than adjacent sections of the first fiber.

The filtered portions 414, 416 can be covers or layers of material formed on the diffusing layer 410 or directly on the bare fiber core and which are configured to emit a particular wavelength or spectrum of light. For example, the filtered portions 414, 416 can comprise translucent covers, such as translucent polymeric sheaths. Each translucent cover can be configured to emit light of a particular wavelength, that is, to emit a particular color. In particular embodiments, the first filtered portions 414 can be configured to emit a first wavelength of light and the second filtered portions 416 can be configured to emit a second wavelength of light. For ease of description, the first filtered portions 414 will be described as emitting a green light and the second filtered portions 416 will be described as emitting a red light, however, it should be noted that any colors can be used provided the receiving element 312 can differentiate between the wavelengths emitted by the first and second filtered portions.

In some embodiments, the light source 310 can be configured to emit broad spectrum light that can be filtered by the first and second filtered portion 414, 416 to emit only a particular wavelength of light. In other embodiments, the light source can be configured to emit only particular wavelengths of light to propagate through the first fiber 316.

In the illustrated embodiment, the portions 412, 414, 416 are arranged in the following repeating pattern: a marked portion 412, which is followed by a first portion 414, which is followed by a second portions 416 moving in a distal-to-proximal direction. However, in other embodiments, the portions can be arranged in any preselected order. For example, a marked portion 412, followed by a second portion 416, followed by a first portion 414. In the illustrated embodiment, the pattern extends along substantially the entire length of the distal end portion 401a of the first fiber 401. However, in other embodiments, the pattern can extend along a portion of the distal end portion 401a.

Each marked portion 412 and each first and second filtered portion 414, 416, can have a predetermined length. For example, each marked portion 412 can have a first length $L_1$, each first filtered portion 414 can have a second length $L_2$, and each second filtered portion 416 can have a third length $L_3$. In some embodiments, $L_1$, $L_2$, and $L_3$ can be equal. In other embodiments, $L_1$ can be greater than $L_2$ which can be equal to $L_3$, or $L_2$ can be greater than $L_3$ which can be greater than $L_1$, etc.

As the first fiber 401 moves axially (e.g., in a proximal or distal direction as shown by arrow 418), the marked portions 412 and first and second filtered portions 414, 416 will align with the recess 406 in a particular order thereby creating a pattern of "flashes" or "blinks" of lights which are transmitted to the receiving element 312 via second fiber 403. The receiving element 312 detects the pattern of blinks and the control unit 360 can use the pattern to calculate the current diameter of the prosthetic valve 100. As mentioned previously, one or more portions can be aligned with the recess simultaneously (see e.g., FIG. 11). When two portions are aligned with the recess, both portions can affect the light emitted by the distal end portion 401a. For example, if a marked portion 412 and a filtered portion 414, 416 are both aligned with the recess 406, the light emitted by the filtered portion 414, 416 will be dimmer than if only the filtered portion 414, 416 were aligned with the recess. As mentioned previously, the control unit 360 can be configured to filter out the dimmer lights and count only each full "flash" or "blink" of light. In other words, the control unit 360 counts the number of times that a filtered portion 414, 416 is fully exposed to the recess while ignoring the times that a filtered portion 414, 416 is only partially exposed to the recess based on the brightness of light.

In some embodiments, if a portion 414, 416 extends partially over the recess, the control unit 360 can determine the length of a portion 414, 416 that is aligned with the recess based on the brightness of the light received by the receiving element 312. In this way, the control unit 360 can calculate the full length of movement of the first fiber 401 relative to the housing 402 at any point in time.

For example, as shown in FIG. 11, first and second filtered portions 414a, 416a can be aligned with the recess 406. Accordingly, both green and red light can be emitted into the recess 406 and transmitted through the second fiber 318 to the receiving element 312. If the first fiber 401 moves proximally (e.g., as the prosthetic valve 100 is radially expanded), the second filtered portion 416a no longer aligns with the recess 406, and only green light is transmitted through the second fiber 403 to the receiving element 312. The receiving element 312 and/or the control unit 230 can determine the direction of movement of the fiber 401 based on which portion comes next in the sequence. Based on the transition from red/green light emission to green light emission, the receiving element 312 and/or the control unit 360 can determine that the first fiber 401 is moving in a proximal direction. Alternatively, if the first fiber 401 moves distally (e.g., as the prosthetic valve 100 is radially compressed), the first filtered portion 414a no longer aligns with the recess 406 and only red light is transmitted through the second fiber 403 into the receiving element 312. Based on the transition from red/green light emission to red light emission, the receiving element 312 and/or the control unit 360 can determine that the first fiber 316 is moving in a distal direction.

The receiving element 312 can determine the relative axial movement $R_3$ between the first fiber 401 and the sensor 400 using the number of blinks and the direction of movement of the fiber. For example, the amount of movement in a first direction (e.g., proximally) can be determined by multiplying the number of blinks in the first direction by the length of each portion 412, 414, 416 that passes the recess 406 travelling in the first direction. The amount of movement in a second direction (e.g., distally) can be determined by multiplying the number of blinks in the first direction by the length of each portion 412, 414, 416 that passes the recess 406 travelling in the second direction. The amount of movement in the second direction can be subtracted from the amount of movement in the first direction in order to determine the relative axial movement of the first fiber 401 relative to the housing 402 in the first direction.

In some particular embodiments, the relative movement $R_3$ of the first fiber 401 relative to the sensor 400 can be calculated according to the equation:

Equation 6: $R_3=(n_1 (L_1+L_2+L_3)-n_2 (L_1+L_2+L_3))$; where $R_3$=relative axial movement between the first fiber and the sensor; $n_1$=number of blinks in a first direction; $n_2$=number of blinks in a second direction; $L_1$=length of each marked portion; $L_2$=length of each first filtered portion; and $L_3$=length of each second filtered portion.

The relative movement $R_3$ can be subtracted from the starting height H of the prosthetic valve 100 (see e.g., FIG. 3) in its radially compressed configuration in order to calculate the current and/or expanded height h (see e.g., FIG. 4) of the prosthetic valve 100 according to the following equation:

Equation 7: $h=(H-R_3)$; where h=current/expanded height of the valve; H=crimped height of valve; and $R_3$=relative axial movement between the first fiber and the sensor.

The expanded height h can be used to calculate the current diameter d (see e.g., FIG. 4) of the prosthetic valve 100 using Equation 2 described above.

As discussed previously, the receiving element 312 can be operatively coupled to a control unit, such as control unit 360 comprising a display, via one or more wires or cables and/or via a wireless communication link. The control until 360 can be configured to continuously calculate the diameter of the prosthetic valve 100 based on the measurement inputs provided by the sensor 400 and to display the diameter of the prosthetic valve 100 on the display in real-time as the prosthetic valve 100 is expanded during an implantation procedure. During the implantation procedure, a physician can monitor the diameter d of the valve to determine when the prosthetic valve is at the diameter that best fits the native annulus.

In a particular example, the relative movement of the first fiber 401 in the proximal direction can be determined using the following exemplary method. A distal end portion of a delivery apparatus 300 comprising sensor 400 (along with radially compressed prosthetic valve 100) can be advanced through the vasculature of a patient to a selected implantation site (e.g., the native aortic annulus). Once the prosthetic valve 100 is positioned at the selected implantation site, a user can actuate the handle 304 of the delivery apparatus 300 to move the second actuator 308 proximally and/or to move the first actuator 306 distally to cause radial expansion of the frame 102. For example, moving the second actuator 308 proximally toward the outflow end of the frame, while holding the first actuator 306 in a fixed position or moving the first actuator distally toward the inflow end of the frame 102 can cause the frame to foreshorten axially and expand radially.

When the prosthetic valve is in the radially compressed configuration, one or more portions of the distal end portion 401a can be aligned with the recess 406. As the second actuator 308 moves proximally, the first fiber 401 also moves proximally, such that the portions of the distal end portion 401a move relative to the recess 406. As each portion or pair of portions aligns with the recess 406, light (or the absence of light) is transmitted to the receiving element 312 via the second fiber 403. The control unit 360 can use the pattern of light detected by the receiving element 312 and the above-described equations to determine the current diameter of the prosthetic valve 100 throughout the implantation process.

In some cases, once the prosthetic valve 100 has been at least partially expanded the physician can determine whether the prosthetic valve needs to be repositioned and/or deployed to a smaller diameter. In such cases, the physician can actuate the second actuator 308 in a distal direction to re-compress or partially re-compress the prosthetic valve 100. As the second actuator 308 moves distally, the first fiber 401 can move distally such that the portions 412, 414, 416 of the distal end portion 401a move distally relative to the recess 406. As each portion or pair of portions aligns with the recess 406, light (or the absence of light) is transmitted to the receiving element 312 via the second fiber 403. The control unit 360 can use the above-described equations to take the distal movement of the second actuator 208 into account when calculating the diameter of the prosthetic valve. Accordingly, the prosthetic valve diameter measurement can be more accurate because it accounts for radial expansion and compression of the valve.

In alternative embodiments, the second fiber 318 of the measurement device can be coupled to the light source 310 and can be used to transmit light into the housing 322, while the first fiber 316 can be coupled to the receiving element 312 and can be used to transmit light from the housing to the receiving element 312. In use, the actuator assembly of the delivery apparatus is operated in the same manner as described above to produce relative axial movement between the first fiber 316 and the housing 322, but the light pattern is produced by the different sections 348, 350 of the first fiber becoming exposed to light emitted into the recess 332 by the second fiber. In this manner, the receiving element 312 detects a flash of light each time a section 350 moves above the recess 332. Similarly, the embodiment of FIGS. 11-12 can be operated by using the second fiber 403 to transmit light into the housing and the first fiber to transmit a pattern of light from the housing to the receiving element 312.

Although the disclosed embodiments pertain generally to delivery apparatuses and methods for implantation of prosthetic heart valves in the native aortic valve, it should be understood that the disclosed embodiments can be used to implant prosthetic devices at any location of the heart or elsewhere in the body. Additionally, although the disclosed embodiments pertain generally to transfemoral delivery of prosthetic devices, it should be understood that the disclosed embodiments can be adapted for use with, for example, transapical procedures, transaortic procedures, trans-subclavian procedures, transradial procedures, or trans-septal procedures.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, a measurement device as shown in FIG. 5 or a measurement device as shown in FIG. 8 or FIG. 11 can be used in combination with prosthetic valve 10. In another embodiment, a measurement device as shown in FIG. 5 can be used in combination with a measurement device as shown in FIG. 8 and/or in FIG. 11.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A medical assembly, comprising:
a prosthetic heart valve that is radially expandable and compressible between a radially compressed configuration and a radially expanded configuration; and
a delivery apparatus comprising:
a handle,
at least one first actuator extending from the handle and coupled to a proximal end portion of the prosthetic heart valve, wherein the at least one first actuator is configured to apply a distally directed force to the proximal end portion of the prosthetic valve;
at least one second actuator extending from the handle and coupled to a distal end portion of the prosthetic valve, wherein the at least one second actuator is configured to apply a proximally directed force to the distal end portion of the prosthetic valve;
a sensor disposed within the handle;
a first motion-transmitting member having a distal end portion coupled to the at least one first actuator and a proximal end portion coupled to the sensor; and
a second motion-transmitting member having a distal end portion coupled to the at least one second actuator and a proximal end portion coupled to the sensor;
wherein the prosthetic heart valve is radially expandable from the radially compressed configuration to the radially expanded configuration upon actuating the at least one first actuator and the at least one second actuator to apply the distally directed force and the proximally directed force, respectively, to the prosthetic heart valve;
wherein the at least one first actuator causes the first motion-transmitting member to move longitudinally in a distal direction relative to the handle when the at least one first actuator is actuated to apply a distally directed force to the proximal end portion of the prosthetic valve;
wherein the at least one second actuator causes the second motion-transmitting member to move longitudinally in a proximal direction relative to the handle when the at least one second actuator is actuated to apply a proximally directed force to the distal end portion of the prosthetic valve;
wherein the sensor senses relative longitudinal movement between the first and second motion-transmitting members in the proximal and distal directions upon actuation of the at least one first actuator and the at least one second actuator to determine the diameter of the prosthetic heart valve as it is expanded.

2. The medical assembly of claim 1, wherein the sensor is a linear displacement sensor.

3. The medical assembly of claim 2, wherein the linear displacement sensor comprises a linear variable differential transformer (LVDT), an optical linear encoder, a linear potentiometer, an optical sensor, a capacitive sensor, or combinations thereof.

4. The medical assembly of any of claims 1-3, further comprising a load cell disposed within the handle and coupled to a proximal end portion of the at least one second actuator, wherein the load cell is configured to measure tensile force in the second actuator as the prosthetic valve expands.

5. The medical assembly of claim 4, wherein the load cell is selected from the group consisting of: a compression load cell, a strain gauge load cell, a piezoelectric load cell, a pneumatic load cell, a hydraulic load cell, or combinations thereof.

6. The medical assembly of any of claims 1-3, further comprising a control unit in communication with the sensor, wherein the control unit is configured to calculate at least one of the real-time radial force and the real-time diameter of the prosthetic valve.

7. The medical assembly of claim 6, wherein the control unit comprises a display configured to display to a user at least one of the real-time radial force and the real-time diameter of the prosthetic valve.

8. The medical assembly of claim 6, wherein the control unit is configured to control the first and second actuators to expand the prosthetic valve according to a preprogrammed expansion algorithm.

9. The medical assembly of any of claims 1-3, wherein the prosthetic heart valve has at least one push-pull actuator assembly comprising a first member attached to the proximal end portion of the prosthetic heart valve and a second member attached to a distal end portion of the prosthetic heart valve, and wherein the at least one first actuator is releasably coupled to the first member and the at least one second actuator is releasably coupled to the second member.

10. The medical assembly of any of claims 1-3, wherein the at least one second actuator extends through the at least one first actuator.

11. The medical assembly of any of claims 1-3, wherein the first and second motion-transmitting members comprise first and second wires.

12. The medical assembly of any of claims 1-3, wherein the first and second motion-transmitting members extend the majority of the lengths of the first and second actuators, respectively.

13. The medical assembly of claim 12, wherein the distal end portions of the first and second motion-transmitting members are affixed to the first and second actuators, respectively, at respective locations adjacent the prosthetic heart valve.

14. A delivery apparatus for a prosthetic heart valve, comprising:
a handle;
at least one first actuator and at least one second actuator extending from the handle, the first actuator being configured to apply a distally directed force to a proximal end portion of a prosthetic heart valve and the second actuator being configured to apply a proximally directed force to a distal end portion of the prosthetic heart valve to radially expand the prosthetic heart valve;
a sensor disposed within the handle;
a control unit in communication with the sensor;
a first motion-transmitting member having a distal end portion coupled to the at least one first actuator and a proximal end coupled to the sensor, wherein distal longitudinal movement of the at least one first actuator causes the first motion-transmitting member to move in a distal longitudinal direction relative to the handle;
a second motion-transmitting member having a distal end portion coupled to the at least one second actuator and a proximal end coupled to the sensor, wherein proximal longitudinal motion of the at least one second actuator causes the second motion-transmitting member to move in a proximal longitudinal direction relative to the handle;
wherein the sensor senses relative longitudinal movement between the first and second motion-transmitting members in the proximal and distal directions upon actuation of the at least one first actuator and the at least one second actuator and the control unit determines the real-time diameter of the prosthetic heart valve as it expands from a radially compressed configuration to a radially expanded configuration based on the relative movement between the first and second motion-transmitting members.

15. The delivery apparatus of claim 14, wherein the sensor is a linear displacement sensor.

16. The delivery apparatus of claim 14 or 15, further comprising a load cell operatively coupled to the second actuator, the load cell configured to measure tension in the second actuator as the prosthetic valve expands.

17. The delivery apparatus of any of claim 14 or 15, wherein the control unit is configured to calculate the real-time radial force of the prosthetic valve based on the tension of the second actuator.

18. The delivery apparatus of claim 17, wherein the control unit further comprises a display configured to display to a user at least one of the real-time radial force and the real-time diameter of the prosthetic valve.

19. The delivery apparatus of any of claim 14 or 15, wherein the first and second motion-transmitting members comprise first and second wires extending the majority of the lengths of the first and second actuators.

20. A method of implanting a prosthetic heart valve, comprising:
inserting into the body of a patient a distal end portion of a delivery apparatus and a prosthetic heart valve coupled to the distal end portion of the delivery apparatus in a radially compressed configuration, the delivery apparatus comprising a handle, at least one first actuator extending from the handle and configured to apply a distally directed longitudinal force to the proximal end portion of the prosthetic valve, at least one second actuator extending from the handle and configured to apply a proximally directed longitudinal force to the distal end portion of the prosthetic valve, a sensor disposed within the handle, a first motion-transmitting member having a distal end coupled to the at least one first actuator and a proximal end coupled to the sensor, and a second motion-transmitting member having a distal end coupled to the at least one second actuator and a proximal end coupled to the sensor;
advancing the delivery apparatus distally until the prosthetic valve is disposed at a selected implantation site;
radially expanding the prosthetic heart valve by at least one of advancing the first actuator distally and retracting the second actuator proximally, wherein the longitudinal distal movement of the at least one first actuator causes the first motion-transmitting member to move longitudinally in a distal direction relative to the handle and wherein the longitudinal proximal movement of the at least one second actuator causes the second motion-transmitting member to move longitudinally in a proximal direction relative to the handle; and
as the prosthetic heart valve is expanded, measuring with the sensor the relative longitudinal displacement between the proximal end portions of the first and second motion-transmitting members in the proximal and distal directions and calculating a real-time diameter of the prosthetic heart valve based on the relative displacement between the first and second motion-transmitting members.

21. The method of claim 20, further comprising as the prosthetic heart valve is expanded, measuring the radial force of the prosthetic valve against surrounding tissue using a load cell coupled to at least one of the at least one first actuator and the at least one second actuator.

22. The method of claim 20 or 21, further comprising displaying at least one of the real-time diameter and the radial force of the prosthetic heart valve on a display unit.

23. A delivery apparatus for a prosthetic heart valve, comprising:
a handle;

at least one first actuator and at least one second actuator extending from the handle, the first actuator being configured to apply a distally directed longitudinal force to a proximal end portion of a prosthetic heart valve and the second actuator being configured to apply a proximally directed longitudinal force to a distal end portion of the prosthetic heart valve to radially expand the prosthetic heart valve;

a load cell operatively connected to a proximal end portion of the first actuator and a proximal end portion of the second actuator and configured to measure a load on at least one of the first actuator and the second actuator by measuring tension in the second actuator as the prosthetic heart valve expands; and a control unit in communication with the load cell and configured to calculate the radial force applied by the prosthetic heart valve against surrounding tissue based on the load measured by the load cell.

24. The delivery apparatus of claim 23, further comprising:

a sensor in communication with the control unit;

a first motion-transmitting member having a distal end portion coupled to the at least one first actuator and a proximal end coupled to the sensor;

a second motion-transmitting member having a distal end portion coupled to the at least one second actuator and a proximal end coupled to the sensor;

wherein the sensor senses relative longitudinal movement between the first and second motion-transmitting members upon actuation of the at least one first actuator and the at least one second actuator and the control unit determines the real-time diameter of the prosthetic heart valve as it expands from a radially compressed configuration to a radially expanded configuration based on the relative movement between the first and second motion-transmitting members.

* * * * *